(12) United States Patent
Van Ooyen et al.

(10) Patent No.: US 7,033,627 B2
(45) Date of Patent: *Apr. 25, 2006

(54) PRODUCTION OF ENZYMES IN SEEDS AND THEIR USE

(75) Inventors: Albert Johannes Joseph Van Ooyen, Voorburg (NL); Krijn Rietveld, Vlaardingen (NL); Wilhelmus Johannes Quax, Voorscheten (NL); Jan Pen, Leiden (NL); Andreas Hoekema, Oegstgeest (NL); Peter Christiaan Sijmons, Amsterdam (NL); Teunis Cornelis Verwoerd, Leiden (NL)

(73) Assignees: Syngenta Mogen B.V., Leiden (NL); Gist-Brocades N.V., Delft (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/149,310

(22) Filed: Feb. 2, 1998

(65) Prior Publication Data

US 2004/0088750 A1    May 6, 2004

Related U.S. Application Data

(60) Continuation-in-part of application No. 08/626,554, filed on Apr. 2, 1996, now Pat. No. 5,714,474, which is a division of application No. 08/146,422, filed on Nov. 2, 1993, now Pat. No. 5,543,576, which is a continuation-in-part of application No. 07/756,994, filed on Sep. 11, 1991, now abandoned, which is a continuation-in-part of application No. 07/498,561, filed on Mar. 23, 1990, now abandoned.

(30) Foreign Application Priority Data

Mar. 25, 1991  (EP) .............................. 91200688

(51) Int. Cl.
*A21D 8/04* (2006.01)
*A21D 2/00* (2006.01)

(52) U.S. Cl. .................. 426/20; 426/549; 426/622
(58) Field of Classification Search ............... 426/10, 426/93, 18, 28, 20, 44, 549, 622; 800/317, 800/320

See application file for complete search history.

(56) References Cited

U.S. PATENT DOCUMENTS

| 19,210 | A | | 1/1858 | Seitz |
| 109,991 | A | | 12/1870 | Delamarre et al. |
| 579,739 | A | | 3/1897 | Clowes |
| 1,155,531 | A | | 10/1915 | Walker |
| 2,219,368 | A | | 10/1940 | McPherson et al. |
| 3,297,548 | A | | 1/1967 | Ware et al. |
| 3,640,723 | A | | 2/1972 | Uhlig et al. |
| 3,956,517 | A | * | 5/1976 | Curry et al. ............... 426/502 |
| 4,116,770 | A | | 9/1978 | Goering et al. |
| 4,223,023 | A | * | 9/1980 | Furda ........................ 424/180 |
| 4,251,630 | A | | 2/1981 | Pratt et al. |
| 4,277,502 | A | * | 7/1981 | Kurzius ..................... 426/20 |
| 4,327,116 | A | * | 4/1982 | Weith ........................ 426/19 |
| 4,458,017 | A | | 7/1984 | Horwath et al. |
| 4,859,486 | A | | 8/1989 | Douglas |
| 4,894,331 | A | | 1/1990 | Ratzkin |
| 4,946,790 | A | | 8/1990 | Fukuhara et al. |
| 4,990,343 | A | * | 2/1991 | Haarasilta et al. ............ 426/10 |
| 5,844,121 | A | * | 12/1998 | Keller ....................... 800/279 |
| 5,866,118 | A | * | 2/1999 | Berka et al. ............... 424/94.6 |
| 5,948,667 | A | * | 9/1999 | Cheng et al. .............. 435/200 |
| 6,039,942 | A | * | 3/2000 | Lassen et al. .............. 424/94.6 |
| 6,361,808 | B1 | * | 3/2002 | Souppe et al. ............... 426/29 |
| 6,514,495 | B1 | * | 2/2003 | Svendsen et al. .......... 424/94.6 |
| 6,531,648 | B1 | * | 3/2003 | Lanahan et al. ............ 800/278 |
| 6,570,008 | B1 | * | 5/2003 | Broglie et al. ............. 536/102 |

FOREIGN PATENT DOCUMENTS

| DE | 2505594 | 2/1974 |
| DE | 262041 | 11/1988 |
| DE | 275704 | 1/1990 |
| EP | 0380343 | 8/1980 |
| EP | 0120516 | 10/1984 |
| EP | 0159418 | 10/1985 |
| EP | 0176112 | 4/1986 |
| EP | 0179441 | 4/1986 |
| EP | 0193259 | 9/1986 |
| EP | 0224287 | 6/1987 |
| EP | 0249432 | 12/1987 |
| EP | 0255378 | 2/1988 |
| EP | 0287152 | 10/1988 |
| EP | 0318341 | 5/1989 |
| EP | 0321004 | 6/1989 |

(Continued)

OTHER PUBLICATIONS

Pomeranz et al. "Improving breadmaking properties with Glycolipids. II. Improving various protein-enriched products." Cereal Chem. 46: 512-518 (1969).*

(Continued)

*Primary Examiner*—Keith Hendricks
(74) *Attorney, Agent, or Firm*—Mary Kakefuda

(57) ABSTRACT

A method of catalyzing in vitro reactions using seeds containing enhanced amounts of enzymes is disclosed. The method involves adding transgenic, non-wild type seeds, preferably in a ground form, to a reaction mixture, especially a bakery process and allowing the enzymes in the seeds to increase the rate of reaction. By directly adding the seeds to the reaction mixture the method provides a solution to the expensive and problematic process of extracting and purifying the enzyme. Methods of treatment are also provided whereby a subject lacking a sufficient supply of an enzyme is administered the enzyme in the form of seeds containing enhanced amounts of the enzyme.

5 Claims, 13 Drawing Sheets

FOREIGN PATENT DOCUMENTS

| EP | 0346909 | 12/1989 |
|---|---|---|
| EP | 0420358 | 4/1991 |
| WO | WO 87/00865 | 2/1987 |
| WO | WO 97/07299 | 12/1987 |
| WO | WO 89/03887 | 5/1989 |
| WO | WO 89/05859 | 6/1989 |
| WO | WO 89/12386 | 12/1989 |
| WO | WO 90/01551 | 2/1990 |
| WO | WO 90/02484 | 3/1990 |
| WO | WO 90/09436 | 8/1990 |
| WO | 9010076 | 9/1990 |
| WO | WO90/12876 | * 11/1990 |

OTHER PUBLICATIONS

Yaseen et al. "Fortification of balady bread with tomato meal." Cereal Chem. 68: 159-161 (1991).*
Austin et al. Production and field performance of transgenic alfalfa (Medicago sativa L.) expressing alpha-amylase and manganese-dependent lignin peroxidase. Euphytica 85: 381-393 (1995).*
Hart et al. "Regulated inactivation of homologous gene expression in transgenic Nicotiana sylvestris plants containing a defense-related tobacco chitinase gene," Mol. Gen. Genet. 235: 179-188 (1992).*
Pen et al. "Production of active Bacillus licheniformis alpha-amylase in tobacco and its applicaion in starch liquification." Bio/Technol. 10: 292-296 (1992).*
Deng et al. "Expression of soybean-embryo lipoxygenase 2 in transgenic tobacco tissue." Planta 187: 203-208 (1992).*
Whitelam (Agricola 95:66845, 1995).*
Almana (Agricola 95:102, 1994).*
Shahidi (Agricola 96:23023, 1994).*
Stedman's Online Medical Dictionary (1997).*
Bade, J. B., Agrobacterium tumefaciens-Mediated Transformation of Brassica napus, Studies Towards High-Quality Transgenic Plants; Dissertation; Universiteit Leiden, Promotor; Prof. Dr. P.J.J. Hooykaas; Oct. 18, 2001; pp. 12.
Kim, I. B. et al., "Nutritional Value of Coastal Bermuda Grass in Swine" Online Article at <http://mark.asci.ncsu.edu/SwineReports/2001/05maninbae.htm> (visited May 15, 2003).
L. Hoffman et al., Plant Mol. Biol., vol. 11 (1988), pp. 717-729.
T. Ohtani et al., Plant Mol. Biol., vol. 16 (1991), pp. 117-128.
B. Larkins et al., J. Cell Biochem., Supp. O (9 Part C), p. 264 (1985).
C. Dorel et al., Plant Physiology, vol. 86 (4 Suppl.) (1988), p. 84.
R. Devlin, Plant Physiology, 3rd ed., N.Y., D. von Nostrand Co., 1975, p. 553.
R. Freedman et al., Cell, vol. 57 (1989), pp. 1069-1072.
R. Aebersold et al., PNAS, vol. 84 (1987), pp. 6970-6974.
J. Sambrook et al., Molecular Cloning, A Lab. Manual, CSHL Press, Cold Spring Harbor, NY, pp. 11.2-11.19; 11.45-11.49 and 11.52-11.61.
A. Kotovjansky et al., Embo. Journal, vol. 4(3) (1985), pp. 781-785.
G. Kawasaki et al., Biochem. Biophys. Res. Comm., vol. 108 (1982), pp. 1107-1112.
Altenbach et al., Plant Mo. Biol. (1989), 13(5):513-522.
Barker et al., Proc. natl. Acd. Sci. USA (1988) 85(2):458-462.
Bustos et al., Plant Cell (1989) 1(9):839-854.
Casey et al., Plant Mol. Biol. Reporter (1987) 5(2):261-281.
Christen et al., Plant Mol. Biol. Reporter (1987) Supp. 12, Part C, pp. 190 (abstract No. L402).
Ellis et al., Plant Mol. Biol. (1988) 10(3):203-214.
Gibson et al., J. Cell Biochem. (1988) Supp. 12, Part C, pp 192 (abstract No. L407).
Higgins et al., Plant Mol. Biol. (1988) 11(5):683-696.
Hoffman et al., EMBO J. (1987) 6(11):3213-3222.
Krebbers et al., Trends in Biotechnol (1990) 8(1):1-3.
Shotwell et al., The Biochemistry of Plants, vol. 15, (1989), Chap. 7, pp. 297-345.
Sijmons et al., Biotechnology (1990) 8(3):217-221.
Vandekerckhove et al., Biotechnology (1989) 7:929-932.
Voelker et al., Plant Cell (1989) 1(1):95-104.
Derwent Publication "Alerting Abstracts Bulletin", Abstract No. 90-21063/28 (Jan. 31, 1990).
Han et al., J. Agric Food Chem. (1988) 36(2):259-262.
Han, Y.W., J. Agric. Food Chem. (1988), 36(6):1181-1183.
Patent Abstracts of Japan, vol. 9, No. 17 (Jan. 24, 1995).
Jordano et al., Plant Cell (1989) 1(9):855-866.
Hesselman et al., Chem. Abstracts (1986) 105:574 (Abstract No. 132749x).
Broz et al., Chem. Abstracts (1986) 105:569 (Abstract No. 23478n).
Gopaldas et al., Food Science Technol. Abstracts (1989) 21(8):123 (Abstract No. 8 M 19).
Goldberg et al., Cell (1989) 56:149-160.
Dorel et al., J. Cell Biol. (1989) 108:327-337.
Voelker et al., Plant Cell (1989) 1:95-104.
Della-Chioppa et al., Plant Physiol. (1987) 84:865-968.
Perlman et al., J. Mol. Biol. (1983) 167:391-409.
von Helin, G., J. Mol. Biol. (1984) 173:243-251.
Schmülling et al., EMBO J. (1988) 7(9):2621-2629.
Palmiter et al., Cell (1987) 50:435-443.
Williams et al., Cell (1988) 52:121-131.
Dunphy et al., Cell (1988) 55:925-928.
Soloman et al., Cell (1988) 54:738-740.
Jähne et al., Plant Cell Reports (1991) 10:1-6.
Brown et al., J. Cell. Biochem. (1988) Supp. 12C:190.
Christen et al., J. Cell. Biochem. (1988) Supp. 12C:190.
Chu et al., J. Cell. Biochem. (1988) Supp. 12C:190.
Ullah et al., Prep. Biochem. (1987) 17(1).63-91.
Matsuda et al., FEBS Letters (1981) 126(1):111-113.
Jaye et al., Nucl. Acids Res. (1983) 11(8):2325-2335.
Ortlepp et al., Gene (1983) 23:267-276.
Cornellissen et al., Nature (1986) 321:531-532.
Ryan et al., Nucl. Acids Res. (1989) 17(9):3584.
Luerssen et al., Nucl. Acids Res. (1989) 17(9):3585.
Iturriaga et al., Plant Cell (1989) 1:381-390.
Jobling et al., Nature (1987) 325:622-625.
Kay et al., Science (1987) 2326:1299-1302.
Baulcombe et al., Nature (1986) 321:446-449.
Brooks, A.D., J. Bacteriol (1990) 172:6950-6958.
Chrispeels, M.J., Ann. Rev. Plant Physiol. Plant Mol. Biol. (1991) 42:1-24.
Fischoff et al., Biotechnology (1987) 5:807-813.
Perlak et al., Proc. Natl. Acad. Sci. (1991) 88:3324-3328.
Vaeck et al., Nature (1987) 328:33-37.
John et al., Food Science Technol. Abstracts (1889) 21(12): 124 (Abstract No. 12 M 11).
Frazer, et al., Proc. IV Int. Congress Food Sci. and Technol., vol. 1 (1974), pp. 127-129.

* cited by examiner

Polylinker sequence:

5' GGAATTCTGGTACCTCCCGGGAGGATCCATCTTAGAGAGCTCGAGTAAGCTTC 3'
   EcoRI  KpnI   SmaI    BamHI  XbaI  SacI  XhoI  HindIII

```
                                                                              EcoRI
TATTTACGTT CGGTCGGATA ACGGACGGGT TTTCAGTTCG GGTTCGGTTC GGATTTCGGG
TTCCGGATTT ATATGGCCCT AGCCTAAATT CGAGTGTGAC CGTTAATCCG TTATACTACG
ATCTAATCAA AACATGTCTA GATCAAATTT GCAATCTTAT TGCATATTTAT TTTGTCTAAC
AATATTACTA GAAATCTTTG TTTATTACCA ACATTAGTAA AACTATATCT TAACCAAAGT
TGCAGGAGCA GTTCGTTTCA AACGTAATTG CTATAGTGAT GTTATTGTAA ATTTGTTATA
CTGATCAAAT GTAAAGAATA ATACAATTTT ATATATATCT GACAAACAAA TCAGTATATA
TATACAAGAA ATATATATTT TGTCCTATTA CATATGCCTA TCTCAAAGTT GATGTGTAAA
GACATGCAGT TCAATAAGCC ATGCAAATTG AGATGTGTCA AACTCCCTTC GTTAATATGT
GTTTTCTTAC AATGTGAAGC CAAATTAAAT TTTCAGAAGA AGACATAAAG ATAGCAACTC
AAATGAAGTG TAGATTGTAC ATAGTCGACT CTATATACCT GGTTCTTATC TCATTCAATT
TATCCTCAAA AAAATTTATC AACATCTATA CAAATAAGTT CACTATAAAT AGCTTCATCT
                                                    *
                                                                         NcoI
AACTCAGCTG TAAGACCAGA AAAACCACAA CAACTAAGTA AAGAGAAAAT GGCTCGGCTC
TCATCTCTTC TCTCTTTTTC CTTAGCACTT TTGACTTTTC TCCATGGCTC TACAGCTCAA
CAGTTTCCAA ACGACTGTCA GCTAGACCAG CTCAATGCAC TGGAGCCGTC ACACGTACTT
AAGGCTGAGG CTGGTCGCAT CGAGGTGTGG GACCACCACG CTCCTCAGCT ACGTTGCTCT
GGTGTCTCCT TTGTACGTTA CATCATCGAG TCTAAGGGTC TCTACTTGCC CTCTTTCTTT
AGCACCGCGA GGCTCTCCTT CGTGGCCTAAA GGTACGTGAA TCTGATTTTG ATACTATATG
```

FIG. 2A

```
AGTATCGAGA TTCAAATTCG TGATCTTTAA GGTTCAGTCT TTTGAGAAAA GGTGTTGTAGT
AAGTATATCA CTATACACGT GCTAAGGTTT TGATCAAATA CATTATAATA TTTTTTTGTT
TAATTTATAA CCTAAATATA TGGTCGATGT TCACAGAACT GGCACTAAA TTTTTTTTTT
TTGGTTTGTT ACATTATAGG AGAAGGTCTT ATGGGGAGAG TGGTCCTGTG CGCCGAGACA
TTCCAGGACT CATCAGTGTT TCAACCAAGC GGTGGTAGCC CCTTCGGAGA AGTCAGGGC
CAAGGACAAC AAGGTCAGGG CCAAGGCCAC CAAGGTCAAG GCCAAGGACA ACAGGGCCAA
CAAGGTCAGC AAGGACAACA GAGTCAAGGC CAGGGTTTCC GTGATATGCA CCAGAAAGTG
GAGCACATAA GGACTGGGGA CACCATCGCT CAGGGTCCCA GTGTAGCCCA ATGGTCTAC
AACGACGGAA ACCAACCACT TGTCATCGTT TCCGTCCTCG ATTTAGCCAG CCACCAGAAT
CAGCTCGACC GCAACCCAAG GGTATATAAA TAAACAAAAA CCTCAAAAGC AATCAAGGGC
AAATCTCCTT TTTAGCATAT TTCTAAATTT ATATCACAAA AATAGCAATC AAAAACTAAA
ATGACCAAAA TCATACTTTT CTAAGTTTAT CCTTTGAAAA TTTTAATTTT TTTATTTTTC
AAATTTGAAT CTATACGCCC AAACCTCATT TCTCAACCCT AAACCATAAC CCTAATCTAA
ACCTTAAACC CTAAACCCCA AACCCTAAAC CCTAAACCCT AAATCCTAAA CCCCAGCCTT
AAACTCTAAA CCCTAAACCC TAAGTTTGTG ACTTTTGATA AAACATTAAG TGCTATTTG
TGACTTTGAC CTGGTGCTA GTTTGAGAAC ATAAACTTGA TTTAGTGCTA TTTTTGTCTT
TTTCTCATCA TATAACTTCT TTTATAATTA CAGAATATCA AAAATATGGT TTTCTGTTT
ATCTGTAGCC ATTTTACTTA GCCGGAAACA ACCCACAAGG CCAAGTATGG ATAGAAGGAC
GCGAGCAACA GCCACAAAAG AACATCCTTA ATGGCTTCAC ACCAGAGGTT CTTGCTAAAG
CTTTCAAGAT CGATCTTAGG ACAGCGCCAAC AACTTCAGAA CCAGCAAGAC AACCGTGGAA
ACATTATCCG AGTCCAAGGC CCATTCAGTG TCATTAGGCC GCCTTTGAGG AGTCAGAGAC
CGCAGGAGGA AGTTAACGCT TTAGAAGAGA CCATATGCAG CGCGAGGTGC ACCGATAACC
```

FIG. 2B

```
TCGATGACCC ATCTAATGCT GACGTATACA AGCCACAGCT CGGTTACATC AGCACTCTGA
ACAGCTATGA TCTCCCCATC CTTCGCTTCC TTCGTCTCTC AGCCCTCCGT GGATCTATCC
GTCAAAACGC GATGGTGCTT CCACAGTGGA ACGCAAACGC AAACGCGGTT CTCTACGTGA
CAGACGGGGA AGCCCATGTG CAGGTGGTTA ACGACAACGG TGACAGAGTG TTCGACGGAC
AAGTCTCTCA AGGACAGCTA CTTTCCATAC CACAAGGTTT CTCCGTGGTG AAACGCGCAA
CAAGGAAACA GTTCCGGTGG ATCGAGTTCA AGACAAACGC AAACGCACAG ATCAACACAC
TTGCTGGACC AACCTCGGTC TTGAGAGGTT TACCATTAGA GGTCATATCC AATGGGTACC
AAATCTCACT CGAAGAAGCA AGAAGGGTTA AGTTCAACAC GATCGAGACC ACTTTGACGC
                                                        BglII
ACAGCAGTGG CCCAGCTAGC TACGGAGGGC CAAGGAAGGC TGATGCCTTAA GAGCTTACCC
AGTGAACCTC TACTGTAAAA GGAAGTTAAA TAGTAATAAA AAGAGTAATA ATAATGTACG
CAAATGTGAC TGGTTTTGTA GAGGTTTTAG AATGTTACTC CTTTTCTGAA TAAAATAACT
CTTTTCTATC AAGGTTTAGC TAGCTGGGCT AATCTATCAA CTTCATTTTT CGACTACGTC
                     HindIII
TACACATACG TATACGAGAT GCAGGCTTCT CCGAGGATAT AGTGACAGTA TCT
```

FIG. 2C

Oligonucleotide duplex A

```
                  NcoI   BamHI  HindIII
5'GGGTTTTTATTTTAATTTTCTTCAAATACTTCCACCATGGGTAACGGATCCA     3'
3'CCCAAAAATAAAATTAAAAGAAGTTTATGAAGGTGGTACCCATTGCCTAGGTTCGA 5'
```

Oligonucleotide duplex B

```
5'CATGAACTTCCTCAAGAGCTTCCCGTTCCCTTTGTTTTTGGCCAATACTTTGTAGCTGTTACGCATGCTCGAG     3'
3'    TGAAGGAGTTCTCGAAGGGCAAGGGAAATACGGTTATGAAACATCGACAATGCGTACGAGCTC     5'
                                                         SphI XhoI BamHI
```

Oligonucleotide duplex C

```
      SphI         XhoI    PstI  BamHI
5'     CT|CTGGCAGTCCCCGCCTCGAGCCCCTGCAG        3'
3' GTACGA|GACCGTCAGGGGCGGAGCTCGGGGACGTCCTAG    5'
       |ROB12|Mature phytase
       signal
       peptide
```

FIG. 3A

Oligonucleotide duplex D

```
NcoI                                                      XhoI  EcoRV PstI        BglII      HindIII
 ┌──┐                                                      ┌──┐  ┌───┐ ┌──┐        ┌──┐      ┌─────┐
       HisGlySerThrAla│LeuAlaValProAlaSer
5' CATGGCTCTACAGCT    CTGGCAGTCCCCGCCTCGAGGATATCCTGCAGATCTCCCCA           3'
3'      CGAGATGTCGA   GACCGTCAGGGGCGGAGCTCCTATAGGACGTCTAGAGGGGTTCGA       5'
          CruA signal     Mature phytase  Multiple cloning site
          peptide
```

Oligonucleotide duplex E

```
5' AATTCAGATCTCCATGGATCGATGAGCT 3'
3'     GTCTAGAGGTACCTAGCTACCTAC  5'
```

Oligonucleotide duplex F

```
                     HgaI SITE
                     α-AMYLASE
                     ┌────────┐
SphI
┌──┐               CT GCAAATCTTAATGGGACGCTGATG   3'
5'                                                
3' GTACGA CGTTTAGAATTACCCTGCGACTACGTCAT          5'
    PROB12 α-Amylase
    signal
    peptide
```

FIG. 3B

XbaI                                                                           HgaI

TCTAGAGTC  ATGAAACAAC  AAAAACGGCT  TTACGCCCGA  TTGCTGACGC  TGTTATTTGC
                                   PstI                                HgaI
GCTCATCTTC  TTGCTGCCTC  ATTCTGCAGC  AGCGGCGGCA  AATCTTAATG  GGACGCTGAT

GCAGTATTTT  GAATGGTACA  TGCCCAATGA  CGGCCAACAT  TGGAAGCGTT  TGCAAAACGA

CTCGGCATAT  TTGGCTGAAC  ACGGTATTAC  TGCCGTCTGG  ATTCCCCCGG  CATATAAGCG

AACCAGCCAA  GCGGATGTGG  GCTACGGTGC  TTACGACCTT  TATGATTTAG  GGGAGTTTCA

TCAAAAAGGG  ACGGTTCGGA  CAAAGTACGG  CACAAAAGGA  GAGCTGCAAT  CTGCGATCAA

AAGTCTTCAT  TCCCGCGACA  TTAACGTTTA  CGGGGATGTG  GTCATCAACC  ACAAAGGCGG

CGCTGATGCG  ACCGAAGATG  TAACCGCGGT  TGAAGTCGAT  CCCGCTGACC  GCAACCGCGT

AATTTCAGGA  GAACACCTAA  TTAAAGCCTG  GACACATTTT  CATTTTCCGG  GGCGGGCAG

CACATACAGC  GATTTTAAAT  GCCATTGGTA  AGGAAAGGCT  GGAACCGATT  GGGACGAGTC

CCGAAAGCTG  AACCGCATCT  ATAAGTTTCA  TGCCGACATC  GATTATGACC  ATCCTGATGT

TGAAACGGC   AACTATGATT  ATTTGATGTA  GTATGCCAAT  GAACTGCAAT  TGGACGGTTT

CGCAGCAGAA  ATTAAGAGAT  GGGCACTTG   GTATGCCAAT  GAACTGCAAT  TGGACGGTTT

CCGTCTTGAT  GCTGTCAAAC  ACATTAAATT  TCTTTTTTG   CGGGATTGGG  TTAATCATGT

CAGGGAAAAA  ACGGGGAAGG  AAATGTTTAC  GGTAGCTGAA  TATTGGCAGA  ATGACTTGCG

FIG. 5A

```
CGGGCTGGAA AACTATTTGA ACAAACAAA TTTTAATCAT TCAGTGTTTG ACGTGCCGCT
TCATTATCAG TTCCATGCTG CATCGACACA GGGAGGCGGC TATGATATGA GGAAATTGCT
GAACGGTACG GTCGTTTCCA AGCATCCGTT GAAATCGGTT ACATTTGTCG ATAACCATGA
                      SalI
TACACAGCCG GGGCAATCGC TTGAGTCGAC TGTCCAAACA TGGTTTAAGC CGCTTGCTTA
CGCTTTTATT CTCACAAGGG AATCTGGATA CCCTCAGGTT TTCTACGGGG ATATGTACGG
GACGAAAGGA GACTCCCAGC GCGAAATTCC TGCCTTGAAA CACAAAATTG AACCGATCTT
AAAAGCGAGA AAACAGTATG CGTACGGAGC ACAGCATGAT TATTTCGACC ACCATGACAT
TGTCGGCTGG ACAAGGGAAG GCGACAGCTC GGTTGCAAAT TCAGTTTGG CGGCATTAAT
AACAGACGGA CCCGGTGGGG CAAAGCGAAT GTATGTCGGC CGGCAAAACG CCCGTGAGAC
ATGGCATGAC ATTACCGGAA ACCGTTCGGA GCCGGTTGTC ATCAATTCGG AAGGCTGGGG
AGAGTTTCAC GTAAACGGCG GGTCGGTTTC AATTTATGTT CAAAGATAGA AGAGCAGAGA
    BamHI
GGACGGATTT CCTGAAGGAA ATCCGTTTTT TTATTTTGCC CGTCTTATAA ATTTCTTTGA
TTACATTTTA TAATTAATTT TAACAAAGTG TCATCAGCCC TCAGGAAGGA CTTGCTGACA
GTTTGAATCG CATAGGTAAG GCGGGGATGA AATGGCAACG TTATCTGATG TAGCAAAGAA
                                       BclI
AGCAAATGTC TCGAAATCA CGGTATCCCG GGTGATCA
```

FIG. 5B

PRODUCTION OF ENZYMES IN SEEDS AND THEIR USE

CROSS-REFERENCE TO RELATED APPLICATIONS

This application is a continuation-in-part of U.S. Ser. No. 08/626,554, filed 02 Apr. 1996, assigned U.S. Pat. No. 5,714,474, which is a divisional of U.S. Ser. No. 08/146,422, filed 02 Nov. 1993, assigned U.S. Pat. No. 5,543,576, which is a continuation-in-part of U.S. Ser. No. 07/756,994, filed 11 Sep. 1991, abandoned, which is a continuation-in-part of U.S. Ser. No. 07/498,561, filed 23 Mar. 1990 now abandoned. The complete text of '554 parent application (including all figures, tables, supporting nucleotide and amino acid sequences, and original claims thereof) is hereby incorporated by references in its entirety as if fully set forth below.

FIELD OF THE INVENTION

The instant invention pertains to the production of enzymes of interest in the seeds of transgenic plants and the use of the thus-produced seeds in industrial processes, without the need for extraction and/or isolation of the enzyme.

BACKGROUND OF THE INVENTION

A number of industries are using enzymes for their processes. These include detergents, textiles, dairy, food and beverage, feed and other industries.

At the present, enzymes are produced on an industrial scale by fermentation processes or are isolated from plant or animal sources. Microbially produced enzymes include proteases, amylases, cellulases, pectinases, phytases and other. Enzyme production by a fermentation process is highly efficient and production levels of more than 10 grams per liter culture medium can be reached.

The possibility of using transgenic plants as a production system for valuable proteins has been proposed. Examples to date are the production of interferon in tobacco (Goodman et al., 1987), enkephalins in tobacco, *Brassica napus* and *Arabidopsis thaliana* (Vandekerckhove et al., 1989), antibodies in tobacco (Hiatt et al., 1990) and human serum albumin in tobacco and potato (Sijmons et al., 1990).

In practice, the transformation of an increasing number of plant species, especially dicotyledonous species (e.g. tobacco, potato, tomato, *Petunia, Brassica*), has become a routine procedure for workers skilled in the art (Klee et al., 1987; Gasser & Fraley, 1989). Strategies for the expression of foreign genes in plants have become well established (Gasser & Fraley, 1989). Regulatory sequences from plants genes have been identified that are used for the construction of chimeric genes that can be functionally expressed in plants and plant cells.

For the introduction of gene constructions into plants, several technologies are available, such as transformation with *Agrobacterium tumefaciens* or *Agrobacterium rhizogenes*. Using this strategy, a wide variety of plant tissues have been exploited, the choice being largely dependent on the plant species and its amenability in tissue culture. Successful examples are the transformation of protoplasms, microspores or pollen, and explants such as leaves, stems, roots, hypocotyls and cotyls. Furthermore, methods for direct DNA introduction in protoplasts and plant cells or tissues are used such as microinjection, electroporation, particle bombardment and direct DNA uptake (Gasser & Fraley, 1989).

Proteins may be produced to plant seeds using a variety of expression systems. For instance, the use of a constitutive promoter such as the 35S promoter of Cauliflower Mosaic Virus (CaMV) (Guilley et al., 1982) will result in the accumulation of the expressed protein in the seeds, inter alia, of the transgenic plant. Alternatively, use may be made of promoters from genes encoding seed storage proteins. Seed storage proteins are expressed in a highly tissue-specific and stage-specific manner (Higgins, 1984; Shotwell & Larkins, 1989), i.e., the genes are expressed only in seed and only during the stage of seed development.

A seed storage protein (reviewed in Higgins, 1984; Shotwell & Larkins, 1989) is defined as any protein which accumulates in significant quantities (up to 90% of total seed protein) in the developing seed and which on germination is hydrolyzed to provide a nutritional source for the early stages of seedling growth. The proteins are contained in an intracellular compartment called the protein body or storage vacuole. This protein body contains protease inhibitors and creates a protease-free environment. The proteases that degrade the storage proteins become active 3–6 days after germination (Larkins, 1981).

Many seed storage protein genes have been isolated and characterized, as well as their 5' and 3' flanking regions (reviewed by Casey & Domoney, 1987). Examples for the globulins and albumins are the glycinin and conglycinin genes of soybean (Fischer & Goldberg, 1982; Harada et al., 1989), the legumin and vicilin genes from pea (Lycett et al., 1984; Higgins et al., 1988), the 11S field bean gene (Baumlein et al., 1986), the 7S phaseolin gene from *Phaseolus* (Doyle et al., 1986), the cruciferon and napin genes from *Brassica* (Ryan et al., 1989; Scofield & Crough, 1987, Radke et al., 1988), the helianthin gene from sunflower (Vonder Haar et al., 1988; Jordano et al., 1989) and the 2S albumin and cruciferin genes from *Arabidopsis thaliana* (Vandekerckhove et al., 1989; Pang et al., 1988). Other examples may be found in the genes encoding the prolamins and glutelins (Casey & Domoney, 1987). Generally, the storage proteins are encoded by multigene families.

Seed storage protein genes have been transferred to tobacco, petunia and rapeseed (Okamura et al., 1986; Beachy et al., 1984; Sengupta-Gopalan et al., 1985; Higgins et al., 1988; Ellis et al., 1988; Barker et al., 1988, Vandekerckhove et al., 1989; Altenbach et al., 1989). The 5' upstream regulatory region of beta-phaseolin from pea was used to direct the expression of beta-glucoronidase (Bustos et al., 1989), phytohemaglutinin (Voelker et al., 1989), luciferase (Riggs et al., 1989) and zein (Hoffman et al., 1987) in tobacco. The promoter of the *Arabidopsis thaliana* 2S albumin gene was used to direct the expression of a modified 2S albumin from the same species in tobacco, *Brassica napus* and *Arabidopsis thaliana* (Vandekerckhove et al., 1989). The genes mentioned above were expressed in a tissue-specific and developmentally regulated manner, i.e., in seed during seed development. The expression levels in all these reports varied, but reached levels as high as 1.7% of the total seed protein (Voelker et al., 1989). It has been found that cDNA can replace genomic DNA containing introns as the basis for obtaining a functional and stable mRNA in the heterologous expression (Chee et al., 1986). These results demonstrate that a person skilled in the art of plant molecular biology can design strategies for seed-specific expression of a given gene in a target plant species that is amenable to transformation technology.

During seed development of dicots, a large part of the total protein synthesis is directed into the vacuole or the protein bodies of storage parenchyma cells. For regulation of this process, the proteins are generally synthesized as precursor. The precursor proteins are equipped with hydrophobic signal peptides, usually at the N-terminus, that are cleaved off at specific stages. A large number of storage protein signal peptides have been described (Doyle et al., 1986; Pang et al., 1988; Vonder Haar et al., 1988; Iturriaga et al., 1989; Dorel et al., 1989; Voelker et al., 1989; Hattori et al., 1985; Lycett et al., 1983; Smith & Raikhel, 1989).

The general applicability of signal peptides is heterologous expressions systems (e.g., Sigmans et al., 1990; Vitale & Bollini, 1986; Slightom et al. 1986; Della-Cioppa et al., 1987) seems to support the idea that a fusion of a signal peptide with a heterologous "passenger protein" may be used for transporting and processing of the passenger protein. The references suggest that a variety of potential "passenger proteins" are candidates for such an expression system.

However, in spite of the attractiveness and viability of the use of plants as bioreactors, the system up until now is not without difficulties. For the examples described above, the plant is used as a bioreactor and the protein of interest is then isolated from the transgenic plant material, i.e., from the tissues containing the highest levels of the protein of interest. The isolation of the protein of interest from the seeds in which it is produced inherently introduces complications as well as added cost (Krebbers & Vandekerckhove, 1990).

A possible solution to this problem may be to avoid the need to extract the expressed protein from the plant material. East German patent DD 275,704 discloses a construct for the expression of a heat stable beta-glucanase in the ungerminated seeds of transformed barley plants and the use of the seeds in brewing processes. However, a persistent problem in the manipulation of small grain cereal crops has been not only the transformation of the protoplasts of cereal plants but the regeneration of the transformed plants as well, which are not enabled in the patent's disclosure. Thus, it would not be possible to obtain enzyme-containing seeds using the process as described in the publication.

SUMMARY OF THE INVENTION

According to the present invention, seeds containing at least one enzyme of interest are provided, which can be used in food and feedstuffs such as dough or other bakery products as catalysts and for digestive reactions, without the need for first extracting and/or isolating said enzymes.

DNA constructs are provided for the transformation of plants which are, in turn, capable of expression of a variety of enzymes of interest in seeds. The constructs employ signal sequences operably linked to a DNA sequence encoding the desired enzyme to be expressed. Such constructs are under the control of regulatory sequences which are capable of directing the expression of the desired enzymes in seeds.

The present invention also provides for the use of the seeds of transgenic plants as a stable and manageable storage form of enzymes. The enzymes are maintained in a dessicated environment which is low in protease activity and thus are protected against degradation.

Moreover, the use of seeds for the storage of enzymes provides a stable vehicle which is easily packaged and transported, and easily handled during actual use.

The present invention further provides a viable solution to the expensive and problematic process of the extraction of enzymes of interest from the seeds in which they are produced. The enzymes remain stable inside the seed and as such may be used as a replacement for the pure enzyme. This benefit, coupled with the low cost of growing seed-producing plants, provides an economical source of such enzymes. Thus, the present invention allows for the reduction of costs associated with the production, storage and use of a variety of enzymes.

DESCRIPTION OF THE FIGURES

FIG. 2. (SEQ ID NO: 38) Genomic sequence of the seed-storage protein gene cruciferen from *Brassica napus*.

FIG. 3. (SEQ ID NOS 39 & 49, respectively) Synthetic oligonucleotide duplexes used for the various constructions.

FIG. 5. (SEQ ID NO: 50) Genomic sequence of the α-amylase gene of *Bacillus licheniformis* as present in vector pPROM54.

DETAILED DESCRIPTION OF THE PREFERRED EMBODIMENTS

Figure 1:
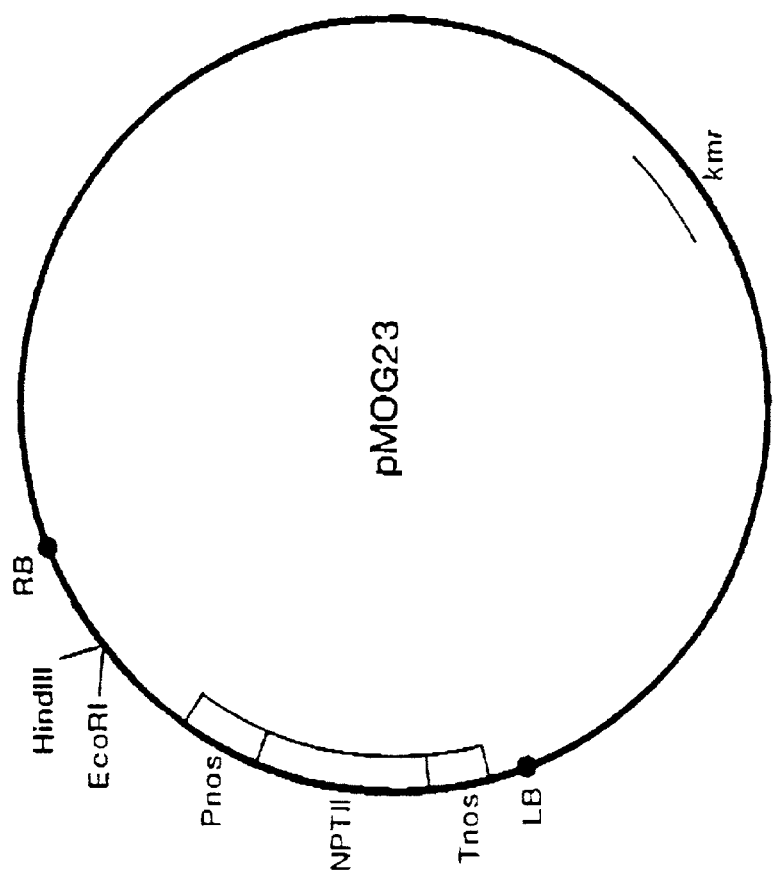
FIG. 1. (SEQ ID NO: 37) Binary vector pMOG23.
Figure 4:
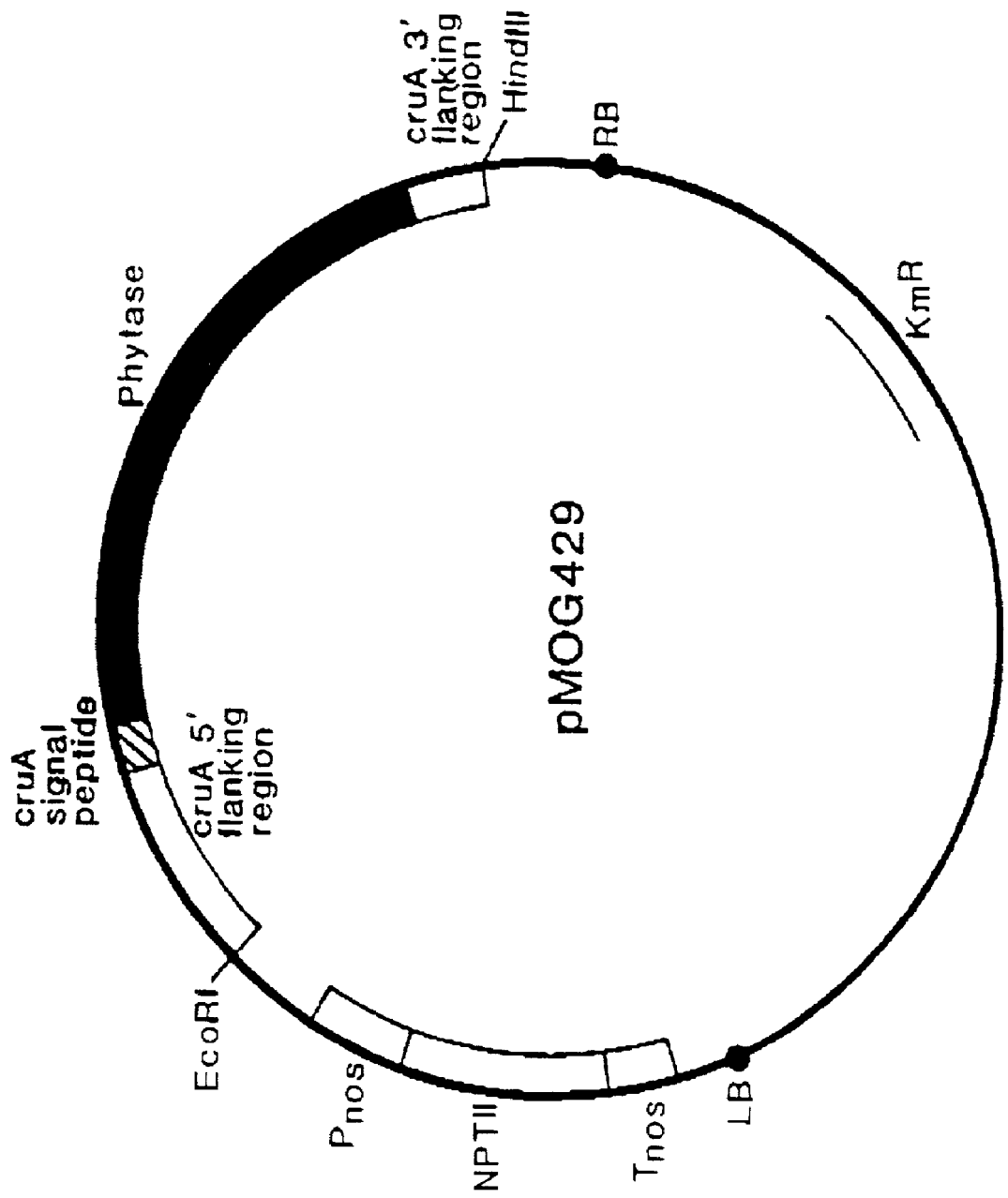
FIG. 4. Plasmid pMOG429. Binary vector pMOG23 containing the cDNA part of phytase encoding the mature enzyme downstream of a DNA sequence encoding the cruciferin signal peptide.

Enzymes of interest which may be produced by the present invention include any enzymes which are capable of use in industrial and food processes such as bakery processes.

The enzymes of interest include enzymes which are heterologous to the plant (i.e. not native to the plant species) in which they are produced. Also intended are enzymes, homologous to the plants (i.e. native to the plant species) in which they are provided, which are overexpressed via recombinant DNA techniques.

Such enzymes are selected from hydrolases such as proteases, cellulases, hemi-cellulases, phosphatases, lipases, pectinases, amylases, lysozymes, pullulaneses and chitinases; lyases such as pectinlyase; isomerases such as glucose isomerase; glucose transferases such as cyclodextrin glycosyl-transferase; and oxygenases such as lipoxygenase.

Preferred enzymes are α-amylase, cellobiohydrolase, cyclodextrin glucanotransferase, endo-glucanase, endo-xylanase, endo-galactanase, lipoxygenase, α-galactosidase, hexose oxidase, arabinanase, protein disulfide isomerase, serine-proteases, chymosin, papain, gastric lipases, pectin lyase and glucose isomerase.

By industrial processes is intended processes in which extracted and/or isolated enzymes are normally included in a reaction mixture, either in vivo or in vitro, containing at least one substrate, wherein the enzymes are capable of catalyzing such reaction of the substrate(s) so as to produce desired effects or products.

Examples of such industrial processes include, but are not limited to, in vitro processes such as the use of phytases in soy processing or in an industrial process such as wet milling or for the production of inositol or inositol-phosphates from phytate. Hemi-cellulases and cellulases may also be used as cell wall degrading enzymes, in general. In a like manner, α-amylases and other enzymes such as xylanases, glucosyl transferases, isomerases and oxygenases may be used in the baking industry to improve the consistency of baked products; α-amylase, amyloglucosidase, xylanases and/or glucose isomerase may be used in starch liquefaction; ligninases and/or xylanases may be used in the paper industry; glucanases, pectinases and/or cellulases may be used in the food and beverage industry, e.g., in fermentation or brewing processes.

Apart from the above-mentioned action of enzymes in in vitro processes, the enzymes stored in seeds may be used to catalyze digestive reactions in vivo. In this manner, the enzymes facilitate the release of nutrients from foodstuffs which otherwise would not be readily available to the animal which ingests them.

Enzymes to be used in such in vivo processes include, but are not limited to, phytases, cellulases, hemi-cellulases, pectinases and amylases. The enzymes as will lead to improved digestion of the foodstuffs. Enzymes as digestive aids can also be used in humans, for instance in illnesses such as cystic fibrosis or other causes of pancreatic insufficiencies. Lipases, proteases, and cellulases contained in seeds may be used as therapeutic additives to alleviate digestive problems associated with such illnesses.

According to the present invention, the desired enzyme is produced in the seeds of transgenic plants. The thus-produced seeds are in turn used in an industrial process which requires the enzyme contained therein, without the need for first extracting and/or isolating the enzyme.

Bakery enzymes can be defined as enzymes especially useful in bakery processes. Such enzymes are, for instance, protein disulfide isomerase, which through a process of breaking and formation of cys-cys bonds in proteins gives improved rheological properties of the dough, more relaxed and better machinability of doughs and a larger volume to the baked product; lipoxygenase-3 (LOX-3) which added to a bread dough results in bleaching of endogenous carotenoids which is desirable in the baking process of white bread and, in addition, strengthens the dough by its oxidizing capacity; cyclodextrin glucano-transferase (CGTase) which when added to a bread dough results in an increase in volume of the baked product and softening of the bread crumb and (endo-)xylanase which results in better dough stability, improved crumb structures and also increases the volume of the baked product.

It will be appreciated by those skilled in the art that seeds containing enzymes for industrial use may be directly used in such processes, or may first be prepared for use by means of grinding to the desired consistency. In either case, the whole or ground seeds may be fed as such into the desired process without the need for further extraction and/or isolation of the enzyme, and also without loss of activity of the enzyme.

It will be appreciated by those skilled in the art that seeds containing enzymes for industrial use may be directly used in such processes, or may first be prepared for such use by means of grinding to the desired consistency. In either case, the whole or ground seeds may be fed as such into the desired process without the need for further extraction and/or isolation of the enzyme, and also without loss of activity of the enzyme.

Transgenic plants, as defined in the context of the present invention, including plants and their progeny, which have been genetically modified to cause or enhance production of at least one enzyme of interest in their seeds. The production of the enzymes of interest is thus increased over the level found in the wild-type plant variety.

In the context of the present invention, the phrase "seeds containing an enhanced amount of enzyme" refers specifically to a statistically significant number of seeds which, on average, contain a statistically significant greater amount of an enzyme as compared with the average amount of enzyme in an equal number of non-modified seeds.

Plant genera which are capable of producing the enzyme of interest in their seed by practice of the present invention include, but are not limited to, *Nicotiana* (e.g., *tabacum*), *Brassica* (e.g., *napus* and *oleracea*), *Arabidopsis*, *Glycine* (e.g., *max*), *Zea* (e.g., *mays*), *Amaranthus*, *Hordeum* (e.g., *vulgarum*), and *Pisum* (e.g., *sativum*), *Juglans* (e.g., *regia*), *Arachis* (e.g. *hypoceae*), *Medicago* (e.g. *sativa*), *Phaseolus* (e.g., *vulgaris*), *Pisum* (e.g. *sativum*), *Triticum* (e.g. *aestivum*), *Panicum* L., *Helianthus* (e.g. *annus*), *Avena* (e.g. *sativa*) and *Oryza* (e.g. *sativa*).

Preferably, the species of choice must have a large production of seed per plant per annum and the chemical and physical properties of the seed should be compatible with the industrial process for which the enzyme is produced. For instance, in some cases when these seeds (after transformation of the parent plant) are to be included in foodstuffs, one may choose a plant species that produces seeds which are low in tannins or other anti nutritional factors. In other cases the ability of the transgenic seeds to be ground to the desired consistency may be the criterion of choice when the seeds are used as additives, e.g., in flour. In yet another embodiment, the seeds containing the enzymes of interest may be directly applied to the desired process (e.g. in feedstuffs), per se, optionally preceded by dehusking and/or drying after harvesting.

The choice of the most suitable plant species can be based on reconstitution experiments. The enzyme of interest can be added together with wild-type seeds to the industrial process for which the transgenic seeds will eventually be produced. In bakery processes seeds which qualify to be added to the dough are seeds of plants which are normally used in baking processes, such as wheat, rye, rice, sunflower, barley, maize and poppy seeds. However, it is also possible to add small amounts of seeds of other plants such as rapeseed.

The genetic modification of the above-described seed-producing plants intends that an expression construct containing a gene encoding an enzyme of interest is introduced into the target plant. This expression construct may include a gene, heterologous to the plant, which is under the control of promoter and termination regions capable of regulating the expression of the gene encoding the enzyme of interest in the seeds of the plant. Also intended is a gene, homologous to the plant which is under the control of a regulatory region capable of effecting the overproduction of the enzyme of interest. By overproduction is intended production of the enzyme of interest at levels above that which is found in the wild-type plant variety.

Transformation of plant species is now routine for an impressive number of plant species, including both the Dicotyledoneae as well as the Monocotyledoneae. In principle any transformation method may be used to introduce chimeric DNA according to the invention into a suitable ancestor cell. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses, in planta *Agrobacterium tumefaciens* mediated gene transfer by infiltration of adult plants of transformation of mature pollen or microspores (EP 0 301 316) and the like. A preferred method according to the invention comprises *Agrobacterium*-mediated DNA transfer. Especially preferred is the use of the so-called binary vector technology as disclosed in EP A 120 516 and U.S. Pat. No. 4,940,838).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or (tissue) electroporation (Shimamoto, et al, 1989, Nature 338, 274–276). Transgenic maize plants have been obtained by introducing the *Streptomyces hygroscopicus* bar-gene, which encodes phosphinothricin acetyltransferase (an enzyme which inactivated the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting embryogenic callus for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice and corn are also amenable to DNA transfer by *Agrobacterium* strains (video WO 94/00977; EP 0 159 418 B1; Gould J. Michael D. Hasegawa O. Ulian EC, Peterson G. Smith R H, (1991) Plant. Physiol. 95, 426–434)

It is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly from callus via organogenesis or embryogenesis and subsequently rooted. Next to the selectable marker, the culture media will generally contain various amino acids and hormones, such as auxin and cytokins. It is also advantageous to add glutamic acid and proline to the medium, especially for such species as corn and alfalfa. Efficient regeneration will depend on the medium, on the genotype and on the history of the culture. If these three variables are controlled regeneration is usually reproducable and repeatable.

The expression of recombinant genes in plants involves such details as transcription of the gene by plant polymerases, translation of mRNA, etc., which are known to persons skilled in the art of recombinant DNA techniques. Only details relevant for the proper understanding of this invention are discussed below.

Regulatory sequences which are known or are found to cause sufficiently high expression (for the purpose of the specific application, as discussed below) of the recombinant DNA in seeds, can be used in the present invention. Such regulatory sequences may be obtained from plants or plant viruses, or chemically synthesized. Such regulatory sequences are promoters active in directing transcription in seeds. These include, but are not limited to, promoters from seed-specific genes, especially those of storage protein genes, such as the cruA promoter of *Brassica napus* (Ryan et al., 1989) or promoters of constitutively expressed genes, such as the 35S promoter of CaMV (Cauliflower Mosaic Virus) (Guilley et al., 1982). Other regulatory sequences are terminator sequences and polyadenylation signals, including every sequence functioning as such in plants; examples are the 3' flanking region of the nopaline synthase gene of *Agrobacterium tumefaciens* or the 3' flanking region of the cruA gene of *Brassica napus*. The regulatory sequences may also include enhancer sequences, such as found in the 35S promoter of CaMV, and mRNA stabilizing sequences such as the leader sequence of Alfalfa Mosaic Virus (AlMV) RNA4 (Brederode et al., 1980) or any other sequences functioning as such.

The protein of interest should be in an environment that allows optimal stability of the protein during seed maturation. The choice of cellular compartments, such as cytosol, endoplasmic reticulum, vacuole, protein body or periplasmic space can be used in the present invention to create such a stable environment, depending on the biophysical parameters of the protein of interest. Such parameters include, but are not limited to, pH-optimum, sensitivity to proteases or sensitivity to the molarity of the preferred compartment. Although homologous signal sequences are preferred, heterologous signal sequences may be used as well. Especially preferred are signal sequences obtained from seed storage proteins.

The seed storage proteins can be divided into four major classes based on solubility characteristics:

1. Albumins—soluble in water and subdivided in two main classes (12S and 2S). The 12S class includes lectins isolated from pea and various beans, e.g., 2S albumins from *Brassica napus, Arabidopsis thaliana, Ricinus communis* (castor bean), *Bertholletia excelsa* (Brazil nut), pea, radish and sunflower.

2. Globulins—soluble in salt solutions and may be either of the 7–8S class like the phaseolins from *Phaseolus*, the vicilins from pea, the conglycinins from soybean, the oat-vicilins from oat and 7S globulins from other species, or of the 11–14S class such as the legumins from pea, the glycinins from soybean, the helianthins from sunflower, the cruciferins from rape or 11–14S proteins from other species such as *Arabidopsia* and bean.

3. Prolamins—soluble in aqueous alcohol, e.g., zeins from corn, the hordeins from barley, the gliadins isolated from wheat and the kafirins from sorghum.

4. Glutelins—soluble in acidic or alkaline solutions and may be isolated from wheat.

Although there are exceptions, the major storage proteins in seed of dicotyledonous plants are globulins, and those of monocotyledonous plants are prolamins and glutelins.

All parts of the relevant DNA constructs (promoters; regulatory, stabilizing, signal or termination sequences) of the present invention may be modified, if desired, to affect their control characteristics using methods known to those skilled in the art. The amount of recombinant protein (the "expression level") needed in the seed should be sufficiently high to use the transgenic seed as a minor additive (on a volume, weight or cost base) in all preferred embodiments of the present invention.

To obtain transgenic plants capable of constitutively expressing more than one chimeric gene, a number of alternatives are available including the following:

A. The use of DNA, e.g. a T-DNA on a binary plasmid, with a number of modified genes coding for the enzymes of interest physically coupled to a second selectable marker gene. The advantage of this method is that the chimeric genes are physically coupled and therefore migrate as a single Mendelian locus.

B. Cross-pollination of transgenic plants each already capable of expressing one or more enzymes of interest, preferably coupled to a selectable marker gene, with pollen from a transgenic plant which contains one or more chimeric genes coding for enzymes of interest coupled to another selectable marker. Afterwards the seed, which is obtained by this crossing, maybe selected on the basis of the presence of the two selectable markers, or on the basis of the presence of the enzymes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes coding for an enzyme of interest and a selectable marker. If the frequency of co-transformation is high, then selection on the basis of only marker is sufficient. In other cases, the selection on the basis of more than one marker is preferred.

D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.

E. Combination of the above mentioned strategies.

The actual strategy may depend on several considerations as maybe easily determined such as the purpose of the parental lines (direct growing, use in a breeding programme, use to produce hybrids) but is not critical with respect to the described invention.

After stable incorporation of the transformed gene sequences into the transgenic plants, the traits conferred by them can be transferred to other plants by sexual crossing. Any of a number of standard breeding techniques can be used, depending upon the species to be crossed.

It is pointed out that seeds containing enhanced amounts of enzymes could be obtained by processes, known to those skilled in the art, other than those recombinant processes mentioned above provided those processes result in obtaining seeds with enhanced amounts of enzymes as compared with the wild-type seeds. For example, it might be possible to obtain such seeds by the use of somaclonal variation techniques. Further, such techniques could be used by themselves or in combination with breeding techniques which employ the concept of cytoplasmic male sterility (Cms) or nuclear male sterility (Nms) (Mariani et al., 1990). Techniques such as somaclonal variation and cross-breeding involving the use of Cms or Nms could be used in combination with the recombinant technologies mentioned above in order to further increase the relative amounts of enzymes present within the seeds. With respect to non recombinant techniques which might be utilized to enhance the amount of enzymes within seeds reference is made to U.S. Pat. No. 4,378,655 issued 7 Apr. 1983 which patent is incorporated herein by reference to disclose such techniques. It is pointed out that there are numerous publications describing breeding techniques involving cytoplasmic male sterility which was discovered by P. LeClercq in 1968 and the corresponding dominant fertility restoring genes (Rf) which were discovered by M. L. Kinmar et al. in 1970. Recently, the use of nuclear male sterility has been described by Mariani et al. in 1990. More generalized disclosures relating to plant breeding are discussed within James R. Welsh "Fundamentals of Plant Genetics and Breeding", 1981 as well as within J. M. Poehlman, "Breeding Field Crops", 1959.

In one embodiment of the present invention, a genomic DNA fragment encoding α-amylase from *Bacillus licheniformis* is placed under the control of the CaMV 35S promoter and enhancer sequences. The mRNA stabilizing leader sequence of RNA4 from A1MV is included, as well as the terminator and polyadenylation signal sequences of the nopaline synthase gene of *Agrobacterium tumefaciens*. The entire construct is thereafter subcloned into a binary vector. This vector is introduced into *Agrobacterium tumefaciens* which contains a disarmed Ti plasmid. Bacterial cells containing this construct are cocultivated with tissues from tobacco plants, and transformed plant cells are selected by nutrient media containing antibiotics and induced to regenerate into differentiated plants on such media. The resulting plants produce seeds that contain and express the DNA construct.

The α-amylase enzyme activity of the transgenic seeds may be determined via methods, not critical to the present invention, such as direct enzyme assays using colorimetric techniques or native gel assays.

The seeds can be used as a source of α-amylase, which can be directly used in industrial processes, such as bakery. Preferably, the seeds are first ground and the entire (ground) mixture may be used in the bakery process, as may be determined by one of ordinary skill in the art.

The following examples are provided so as a to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric.

EXAMPLE 1

Construction of the Binary Vector pMOG23

In this example, the construction of the binary vector pMOG23 (in *E. coli* K12 DH5α, deposited at the Centraal Bureau voor Schmmelcultures on Jan. 29, 1990 under accession number CBS 102.90) is described.

The binary vector pMOG23 (FIG. 1) is a derivative of vector Bin19 (Bevan, M., 1984). To obtain pMOG23, the vector Bin19 is changed in a way not essential for the present invention, using techniques familiar to those skilled in the art of molecular biology.

First, the positions of the left border (LB) and the right border (RB) are switched with reference to the neomycine phosphotransferase gene II (NPTII gene). Secondly, the orientation of the NPTII gene is reversed giving transcription in the direction of LB. Finally, the polylinker of Bin19 is replaced by a polylinker with the following restriction enzyme recognition sites: EcoRI, KpnI, SmaI, BamHI, XbaI, SacI, XhoI, and HindIII.

EXAMPLE 2

Cloning a Seed-Specific Expression Construct

An expression construct is constructed in such a way that seed-specific expression in obtained, using sequences of the *Brassica napus* 12S storage protein gene cruciferin (cruA; Ryan et al., 1989). These sequences may be replaced by those from similar seed-specific genes to achieve the same goal as is the objective of this invention.

For all *E. coli* transformation in this example, *E. coli* K-12 strain DH5α is used.

a) Construction of the Expression Construct

For the construction of the expression construct for seed-specific expression, the promoter and terminator sequences from the cruciferon A (cruA) gene of *Brassica napus* cv. Jet Neuf are synthesized using PCR technology with isolated genomic DNA (Mettler, I. J., 1987) as a template. This gene shows seed-specific expression and its coding and flanking sequences have been determined (Ryan et al., 1989).

Two sets of oligonucleotides are synthesized. One to allow amplification of the cruA 5' flanking region and part of the signal peptide encoding sequence as an EcoRI/NcoI fragment: (SEQ ID NOS 33 & 34, respectively) 5' GTTCG-GAATTCGGGTTCCGG 3' and 5' AACTGTTGAGCTG-TAGAGCC 3'. The other for amplification of the 3' flanking sequence as a BglII/HindIII fragment (SEQ ID NOS 35 & 36, respectively): 5' CTTAAGATCTTACCCAGTGA 3' and 5' CGGAGAAGCTTGCATCTCGT 3'.

The oligo's are designed to contain suitable restriction sites at their termini to allow direct assembly of the expression construct after digestion of the fragments with the restriction enzymes.

The 5' fragment of the cruA gene, that includes 54 nucleotides of the sequence encoding the signal peptide is cloned into vector pMOG445 (Oligonucleotide duplex E (FIG. 3) cloned into vector pUC18, linearized with SstI and EcoRI), cut with EcoRI and NcoI, resulting in vector pMOG424. The synthetic oligonucleotide duplex D (FIG. 3), comprising the final 5 coding triplets for the signal sequence of *Brassica napus* cruciferin, the sequence encoding amino acids 1–6 of mature phytase and a multiple cloning site, is cloned in vector pMOG424 cut with NcoI and HindIII. The resulting vector is called pMOG425. The 3' cruA PCR fragment is cloned as a BglII/HindIII fragment into pMOG425 digested with BGIII and HindIII, resulting in pMOG426.

In this vector the gene of interest can be cloned. The resulting vector is mobilized, in a triparental mating with the *E. coli* K-12 strain RX2013 (containing plasmid pRK2013) (Ditta et al., supra), into *Agrobacterium* strain LBA4404 (Hoekema et al., 1983, supra) which contains a plasmid with the virulence genes necessary for T-DNA transfer to the plant.

EXAMPLE 3

Cloning of the α-amylase Gene of *Bacillus licheniformis* in an Expression Cassette for Constitutive Expression In this example, the α-amylase gene from *Bacillus licheniformis* is tailored and cloned in an expression cassette for constitutive expression which also contains the coding information for a signal peptide sequence of plant origin. As a final step, the entire construct is cloned in a binary vector, transferred to *Agrobacterium tumefaciens* strain LBA4404, which is used to transform the plant of interest. Any other gene or cDNA may be cloned in a similar way as is described here for the α-amylase gene.

All transformations in this example are done in *E. coli* K-12 strain DH5-α.

a) Tailoring of the α-amylase Gene of *Bacillus licheniformis*

The α-amylase gene from *Bacillus licheniformis* (FIG. 5), present in the *Bacillus* vector pPROM54 (deposited at the Central Bureau voor Schimmelcultures on Nov. 5, 1985, under accession number CBS 696.85), is digested with XbaI and BclI. The XbaI/BclI fragment is cloned in plasmid pUC18 linearized with XbaI and BamHI, resulting in plasmid pMOG318. A SalI/BamHI fragment is synthesized using PCR technology with pMOG318 as a template creating the BamHI site by use of a mismatch primer (indicated in FIG. 5). The SalI/BamHI PCR fragment is cloned in plasmid pIC-19R (Marsh et al., 1984) digested with SalI and BamHI, resulting in plasmid pMOG319. The SalI fragment, which contains the 5'end of the α-amylase gene, from pMOG318 (using the SalI site present in pUC18) is cloned in pMOG319 linearized with SalI. This results in plasmid pMOG320 that contains the entire α-amylase gene.

b) Construction of Vector pMOG29

The expression construct of ROK1 (Baulcombe et al., 1986) is cloned as an EcoRI/HindIII fragment into pUC18. This construct contains the Cauliflower Mosaic Virus (CaMV) 35S promoter on an EcoRI/BamHI fragment and the nopaline synthase (nos) transcription terminator on a BamHI/HindIII fragment. The promoter fragment consists of the sequence from −800 to +1 of the CaMV 35S promoter. Position +1, which is included is the transcription initiation site (Guilley et al., 1982). The sequence upstream of the NcoI site at position −512 is deleted and this site is changed into an EcoRI site. This is done by cutting the expression construct present in pUC18 with NcoI, filling in the single-stranded ends with Klenow polymerase and ligation of an EcoRI linker. The resulting plasmid is cut with EcoRI, resulting in the deletion of the EcoRI fragment carrying the sequences of the 35S promoter upstream of the original NcoI site. The BamHI/HindIII fragment, containing the nos terminator is replaced by a synthetic DNA fragment (oligo-nucleotide duplex A, FIG. 3) containing the leader sequence of RNA4 of Alfalfa Mosaic Virus (AlMV) (Brederode et al., 1980). This is done by cleavage with BamHI, followed by cleavage with HindIII and ligation of the synthetic DNA frgment. The BamHI site and three upstream nucleotides are deleted by site-directed mutagenesis. In the resulting plasmid, the BamHI/HindIII fragment containing the nos terminator sequence is reintroduced. The gene encoding α-glucuronidase (originating from plasmid pRAJ 275; Jefferson, 1987) was ligated in as an NcoI/BamHI fragment, resulting in plasmid pMOG14. From the literature it is known that duplication of the sequence between −343 and −90 increases the activity of the 35S promoter (Kay et al., 1987). To obtain a promoter fragment with a double, so-called enhancer sequence, the following steps, known to those skilled in the art, are carried out. From plasmid pMOG14, the enhancer fragment is isolated on an AccI/EcoRI fragment and subsequently blunt-ended with Klenow polymerase. The obtained fragment is introduced in pMOG14 cut with EcoRI and blunt-ended, in such a way that the border between the blunt-ended EcoRI and AccI sites generate a new EcoRI site.

Figure 6:
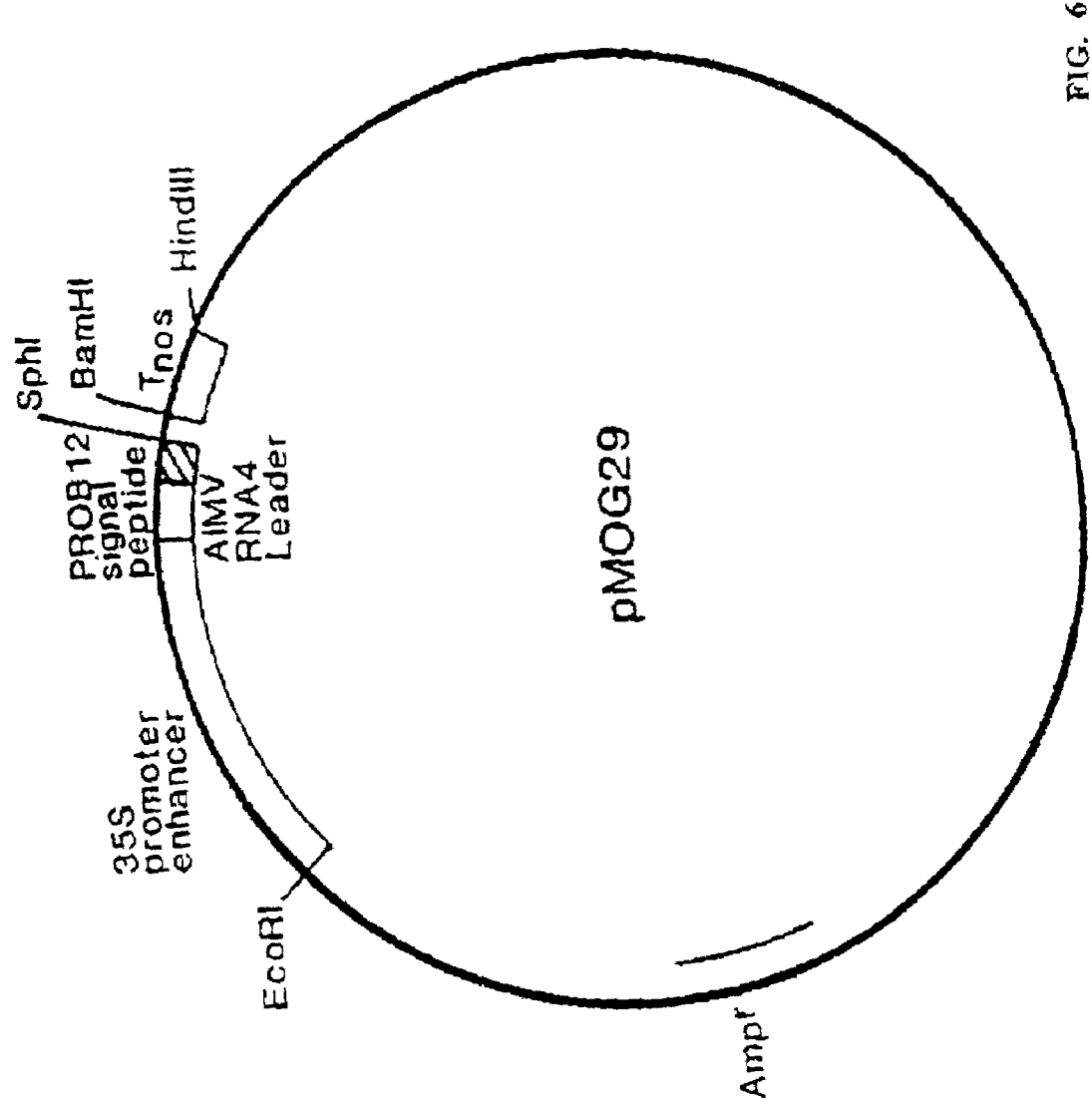
FIG. 6. Plasmid pMOG29. Plasmid pUC18 containing an expression cassette for constitutive expression in plants and a sequence encoding a tobacco signal peptide.
Figure 7:
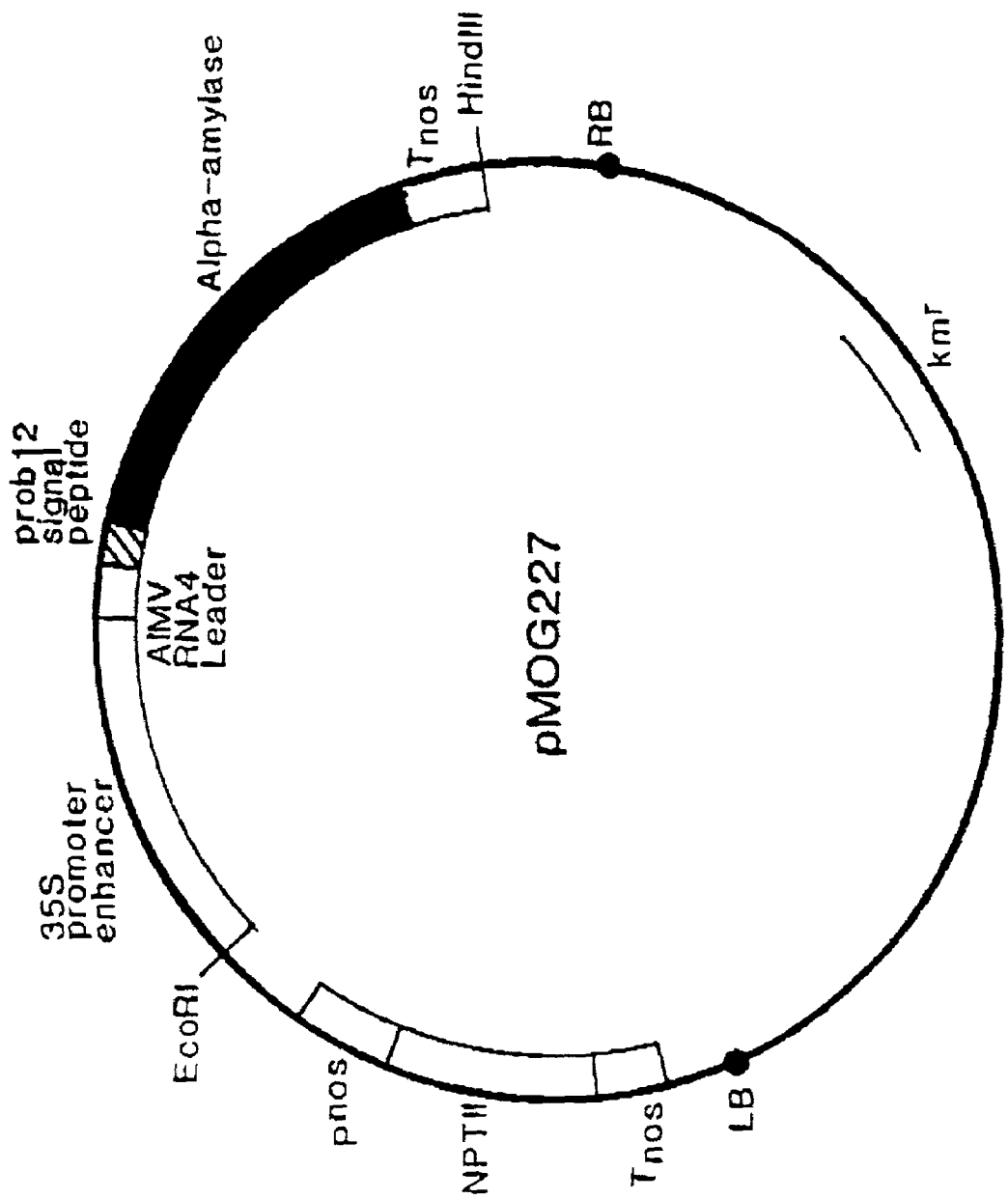
FIG. 7. Plasmid pMOG227. Binary vector containing the part of the α-amylase gene encoding the mature enzyme downstream of a tobacco sequence encoding a signal peptide in an expression cassette for constitutive expression.

The resulting plasmid (pMOG18) contains the 35S promoter with a double enhancer sequence, the leader sequence of RNA4 from AlMV and the nos terminator in an expression construct still present on an EcoRI/HindIII fragment. Finally, the NcoI/BamHI fragment encoding β-glucoronidase is replaced with the synthetic DNA fragment B (FIG. 3), derived from the PROB12 cDNA (Cornelissen et al., 1986). This fragment B encodes the PR-protein PR-S signal peptide sequence from tobacco Samsun NN. An SphI site is created in the signal peptide encoding DNA sequence by changing one nucleotide. This change does not alter the amino acid sequence of the encoded PR-S signal peptide. The resulting plasmid is called pMOG29 (FIG. 6).

c) Cloning of the α-amylase Gene from *Bacillus licheniformis* in the Binary Vector Plasmid pMOG320 is digested with HgaI and BamHI. The HgaI/BamHI fragment, which encodes mature α-amylase from amino acid 9 onward, is cloned in a three-way ligation with the synthetic oligonucleotide duplex F (FIG. 3) into pMOG29 linearized with SphI and BamHI, resulting in plasmid pMOG321. The oligonucleotide duplex has the coding information for the final 2 amino acids of the signal peptide of PR-S and for the first 9 amino acids of mature α-amylase. The entire construct, containing the chimeric α-amylase gene, is inserted as an EcoRI/HindIII into the binary vector pMOG23 linearized with EcoRI and HindIII. The resulting binary plasmid pMOG227 (FIG. 7) is mobilized, in a triparental mating with the *E. coli* K-12 strain RK2013 (containing plasmid pRK2013) (Ditta et al., 1980), into *Agrobacterium* strain LBA4404 that contains a plasmid with the virulence genes necessary for T-DNA transfer to the plant.

EXAMPLE 4

Stable Expression of *Bacillus licheniformis* α-amylase in Tobacco

In this example tobacco is transformed by cocultivation of plant tissue with *Agrobacterium tumefaciens*, containing a binary vector with the chimeric α-amylase gene. Transgenic plants are selected in antibiotic resistance. The seeds of the transgenic plants are assayed for α-amylase activity. High expressors are analyzed more thoroughly and used in further experiments.

*Agrobacterium* strain LBA4404 (pMOG227) is used for transformation experiments. Transformation of tobacco (*Nicotiana tabacum* SR1) is carried out using cocultivation of leaf discs according to the procedure of Horsch et al., (1985). Transgenic plants are regenerated from shoots that grow on selection medium (100 mg/l kanamycin). Young plants are assayed for NPTII-activity, grown to maturity and allowed to self-pollenate and set seed. Seeds from individual transformants are pooled and part of the seed sample is assayed for the presence of α-amylase. From clones with the highest expression levels, compared to untransformed control seeds, the remaining seeds are germinated on kanamycin (200 mg/L) (hence also transgenic for α-amylase) and selected and used for mass propagation of plants capable of producing seeds containing the highest amounts of α-amylase. A maximum α-amylase expression level of 0.4% of the total soluble seed protein was observed. These seeds can then be used, e.g. for digestion experiments.

EXAMPLE 5

Application of α-amylase Formulated in Seeds for the Liquefaction of Starch

*Bacillus licheniformis* α-amylase, expressed in tobacco seed, was applied in the liquefaction of starch as follows: 100 grams of both α-amylase-expressing and control tobacco seeds are harvested. Seeds were ground with a sieve (Retch-mill ZM1) having pores of 250 μm, taking care to keep the seeds cooled. To determine their α-amylase content, the milled seeds were extracted with 10 volumes of 0.5 M glycine buffer pH 9.0 with 10 mM $CaCl_2$ during 30 min at 0_C. The supernatant was used for α-amylase determination by the Phadebas method (Pharmacia Diagnostics). The units are referred to as TAU (thermostable α-amylase units).

Liquefaction tests were carried out as follows: starch slurry (composition: 3.3 kg corn or potato starch, D.S. (Dry Substance) 88% (2.904 kg starch); 5.45 1 $H_2O$;; D.S. of slurry becomes 33%; the pH was corrected to 6.5 with 1 N sulfuronic acid or 1 N NaOH. Either milled seeds or microbial α-amylase were added to an amount equivalent to 4.4 T.A.U./g D.S.) is heated to 100° C. as rapidly as possible and this temperature is maintained for 10 minutes. The slurry is then brought to 95° C. and maintained at that temperature for 2 hours. Afterwards, the samples were acidified with $H_2SO_4$ to obtain pH 3.5 and placed in a boiling water bath for 10 minutes in order to stop enzymatic activity before the DE (dextrose equivalents) and hydrolysis pattern were determined by HPLC. A column of BIORAD HPX-42A was used for HPLC analysis with demineralized water as eluent.

Figure 8C:
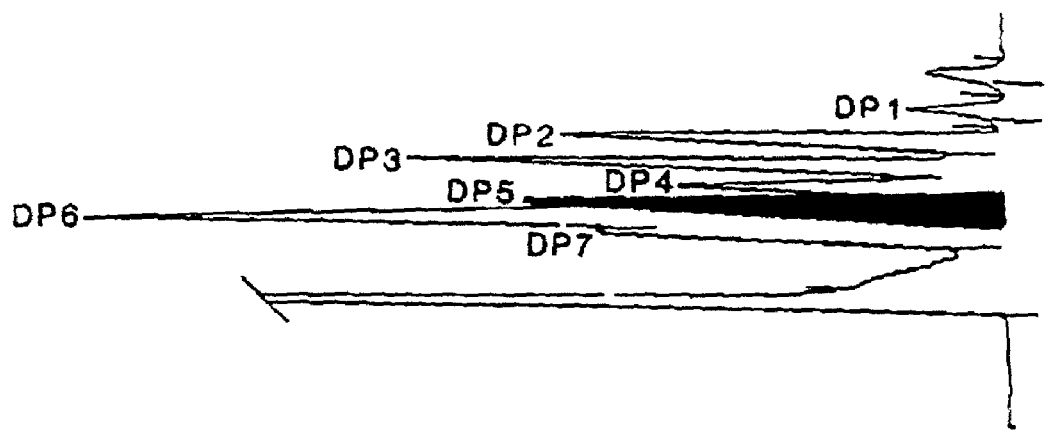
FIG. 8. Comparison of oligosaccharide patterns obtained from the hydrolysis of potato starch using A) tobacco seeds transformed with the gene encoding *Bacillus licheniformis* α-amylase, B) *Bacillus licheniformis* α-amylase and C) *Bacillus amylolicuefaciens* α-amylase.
Figure 8B:
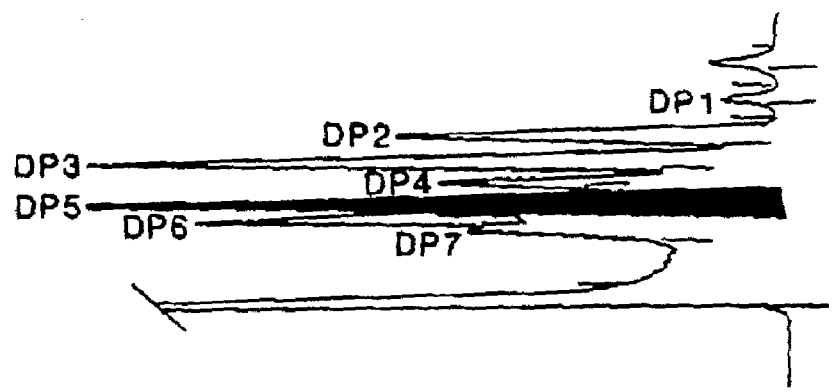
Figure 8A:
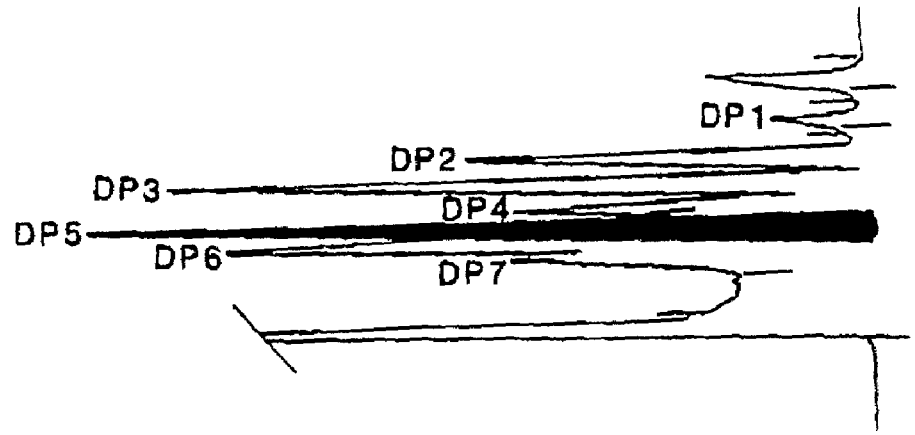
Figure 9C:
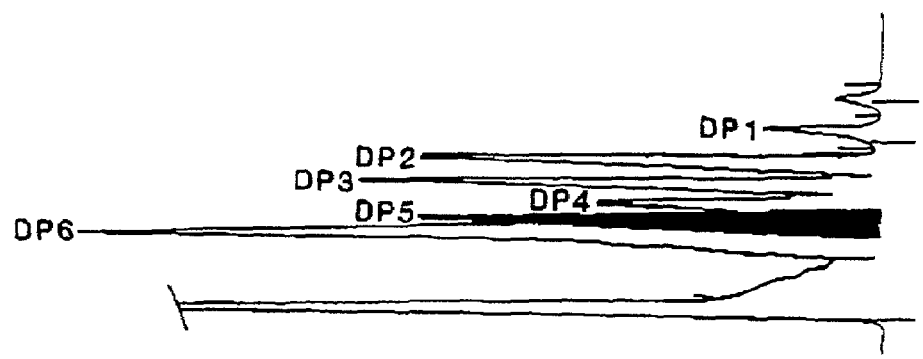
FIG. 9. Comparison of oligosaccharide patterns obtained from the hydrolysis of corn starch using A) tobacco seeds transformed with the gene encoding *Bacillus licheniformis* α-amylase, B) *Bacillus licheniformis* α-amylase and C) *Bacillus amyloliquefaciens* α-amylase.
Figure 9B:
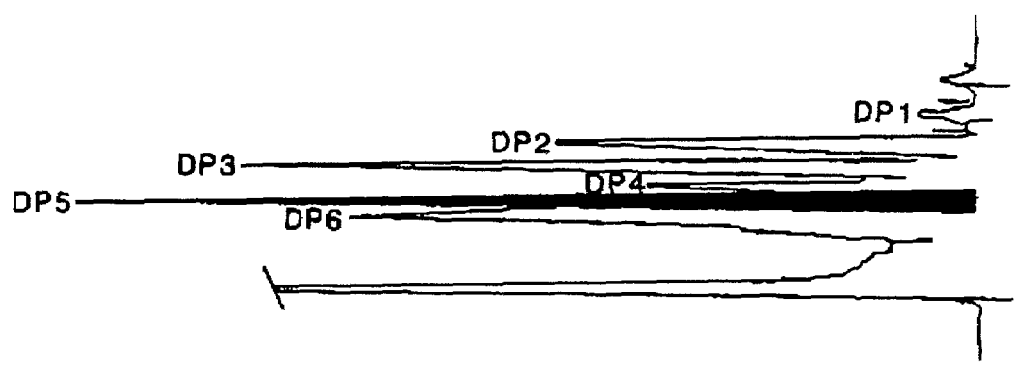
Figure 9A:
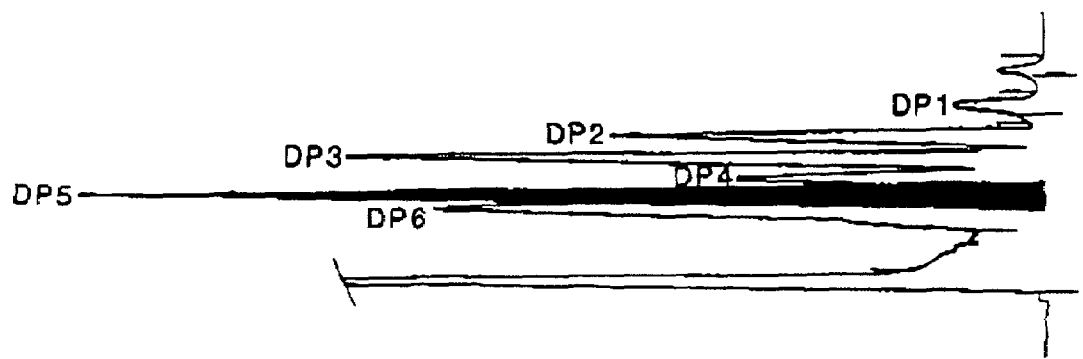

The oligosaccharide pattern obtained from the hydrolysis of potato and corn starch using A) transformed plant seeds; B) Maxamyl® (*Bacillus licheniformis* α-amylase obtained from Gist-brocades N.V., Delft, The Netherlands); and C) Dexlo®CL (*Bacillus amyloliquefaciens* α-amylase from Gist-brocades) were compared (FIGS. 8 and 9). The oligosaccharide pattern obtained from transformed plant seeds and Maxamyl® are identical, yet both differ from that obtained from Dexlo®, confirming that *Bacillus licheniformis* α-amylase is produced in plant seeds. The DE values obtained with the plant seeds (Table 1) are in the commercially acceptable range (DE≧16) (Reilly, 1985).

TABLE 1

Dextrose equivalent (DE) values obtained from hydrolysis of corn and potato starch

|  | Potato Starch DE | Corn Starch DE |
|---|---|---|
| Maxamyl ® WL7000 | 18 | 16 |
| Transformed tobacco seeds | 16 | 13 |
| Non-transformed tobacco seeds | 0 | 0 |
| Dexlo ® CL | 15 | 18 |

EXAMPLE 6

Expression of Protein Disulfide Isomerase (PDI) in *Brassica napus* Seeds

The binary vector pMOG1068 [Cru-A (promoter)-AlMV (leader)-PDI (signal peptide)-PDI (coding sequence +KDEL retention signal)-Cru-A (terminator)-RB] consists of the PDI coding region (and the PDI signal peptide and the KDEL ER retention signal) under control of the Cruciferin A (Cru A) promoter and terminator sequences. An AlMV leader sequence is included. The backbone of the expression construct is the binary vector pMOG800 (a derivative of pMOG23, in which an additional KpnI restriction site was introduced into the polylinker between EcoRI and SmaI). This plasmid contains between the left and right borders of T-DNA a kanamycin resistance gene for selection of transgenic plant cells. A sample of *E. coli* DH5α, harbouring pMOG800, was deposited at the Centraal Bureau voor Schimmelcultures, Oosterstraat 1, Baarn, The Netherlands, on Aug. 12, 1993 under number CBS 414.931. The binary vector was cloned as follows.

The cloning vector pUC28 was made by introducing a synthetic oligo adaptor (SEQ ID NOS 1 & 2,respectively):

```
pUC28 I    5'AATTCAGATCTCCATGGATCGATGAGCT 3' pUC28 II   3'GTCTAGAGGTACCTAGCTAC 5'
``` into the EcoRI and SstI sites of pUC18. This introduces BglII, ClaI, and NcoI sites into the polylinker of pUC18. pUC28 was subsequently linearized with SalI and NcoI.

The Cruciferin A promoter was fused to the AMV leader sequence in a three way ligation in which the (SalI-NcoI) linearized pUC28 vector, a 101 bp SalI-PvuII fragment from the CruA promoter (see Example 2) and the oligo primers (SEQ ID NOS 3 & 4, respectively):

AMV I/AMVII:

```
5'CTGTAAGACCAGAGGGTTTTTATTTTTAATTTTCTTTCACCTAGGTCCAC 3'

3'GACATTCTGGTCTCCCAAAAATAAAAATTAAAAGAAAGTGGATCCAGGTGGTAC 5'
``` were used. The vector was subsequently linearized with NcoI and EcoRI.

The cDNA clone of Protein Disulfide Isomerase (PDI) was isolated from alfalfa (Shorrosh and Dixon 1992, The Plant Journal 2, 51–58) by PCR amplification. Part of the clone was amplified by use of the primers (SEQ ID NOS 5 & 6, respectively:

```
PDI 3:    5'CGC ACC ATG GTG TGG ACA CTG 3'

PDI 4:    5'CTT GAA TAT TCT TTC CAC CAT 3'
```

Hereby a novel NcoI site was introduced at 180 bp downstream of the ATG start codon. The resulting 186 bp NcoI-SspI PCR fragment was cloned together with an internal SspI-EcoRI PDI fragment (1068 bp) into the pUC28 vector already containing the CruA-AlMV leader fusion (and which was linearized with NcoI and EcoRI).

The 5' part of the PDI gene was amplified with the primers (SEQ ID NOS 7 & 8, respectively):

```
PDI 1:    5'CCAACCATGGCGAAAAACGTT 3'

PDI 2:    5'CCACACCATGGTGCGTAGAACTCAACGACG 3'
```

By using these primers a novel NcoI site was created at the ATG start codon of PDI and a novel NcoI site was created at 180 bp downstream of the ATG codon. At the same time an internal EcoRI site at 166 bp downstream of the ATG codon was destroyed. The mutations are all silent.

The 3' part of PDI coding region was amplified with the primers:

```
PDI 5:    5'GACATCATAGAATTCATTGAA 3'

PDI 6:    5'GCGGAGATCTTCAAAGCTCATCTTTTGG 3'
```

This creates a BglII site downstream of the stop codon. The resulting 112 by EcoRI-BglII PCR fragment was used in a three way ligation with the CruA terminator (a 218 bp BglII-XhoI fragment) into pMOG800 linearized with EcoRI and XhoI. The resulting plasmid was linearized with EcoRI and used to clone in the CruA promoter as a 2574 bp EcoRI-SalI fragment and the CruA AMV 5'PDI fusion as a 1586 bp SalI-EcoRI fragment. The resulting binary vector was designated pMOG1068.

The binary vector was finally transferred to *Agrobacterium tumefaciens* strain MOG 301 (Hood et al. 1993, Transgenic Res. 2: 208–218).

Transgenic *Brassica napus* plants were generated by *Agrobacterium* mediated transformation as previously described (Bade and Damm, 1995, *Agrobacterium*-mediated transformation of Rapeseed (*Brassica napus*) In: I. Potrykus and G. Spangenberg (eds.) Gene Transfer to Plants, Springer verlag Berlin).

EXAMPLE 7

Expression of PDI in Rapeseed

S1-seed batches of 12 independent transgenic lines harbouring pMOG1068 were analyzed for the expression of PDI by Western analysis. A cDNA clone encoding the alfalfa PDI was expressed in *E. coli* cells and a polyclonal antiserum was raised against the expressed protein in rabbits (Shorrosh et al., 1993, Plant Physio. 103: 719–726).

Transgenic seeds were homogenized in 50 mM sodium phosphate buffer, pH 7.5, containing 10 mM EDTA, 50 NaCl and 0.1% Triton X-100. The extracts were clarified by centrifugation for 5–10 minutes in an Eppendorf centrifuge. Five μg protein was loaded on a 12.5% SDS-PAA gel. The level of PDI was estimated after Western blotting by a comparison with a series of known quantities of purifed PDI in a wild type canola protein background. The expression level varied between 0 and approximately 0.1% (based on total extractable protein).

EXAMPLE 8

Expression of Lipoxygenase 3 (LOX-3) in *Arabidopsis* Seeds

The binary vector pMOG1011 [β-phaseolin (promoter)-AlMV (leader)-LOX-3 (coding sequence)-Cru-A (terminator)-RB] consists of the LOX-3 coding region under control of the β-phaseolin promoter and the Cruciferin A terminator sequences. The AlMV leader is also included in the construct. The backbone of the expression construct is the binary vector pMOG800 harbouring the NPTII gene under control of the nos promoter and multiple cloning sites between the left and right T-DNA borders. The binary vector was cloned as follows.

The β-Phaseolin promoter was isolated by PCR starting of with genomic DNA isolated from *Phaseolus vulgaris* cv Helda as a template and the primers (SEQ ID NOS 11 & 12):

```
TCV 17:    5'GCGCGAATTCTATACAATGAAAATTTCACC 3'

TCV 18:    5'GCTCTCACCATGGTAGAGTAG 3'
```

The primers were based on the sequence of the β-Phaseolin seed storage protein gene (Gen-Bank accession number J01263, M13758). Herewith a NcoI site was created at the ATG start codon of the β-Phaseolin coding region and an EcoRI site at the 5' end of the promoter. From the resulting PCR fragment a 906 bp EcoRI-ScaI fragment was isolated. This fragment was linked by a three way ligation with a 53 bp PvuII-NcoI fragment isolated from the CruA-AlMV fusion (Example 6) into the cloning vector pUC28 (Example 6) which was linearized with EcoRI and NcoI.

To make the exact fusion of the β-Phaseolin promoter, AlMV leader and the LOX3 cDNA two synthetic adaptors (SEQ ID NOS 13 & 14, respectively) were made (Lox 21 and Lox 22):

```
5'CATGCTTGGGGGTCTTCTCCATAGGGGTCATAAGATAAAAGGTAC 3'

3'GAACCCCCAGAAGAGGTATCCCCAGTATTCTATTTTC 5'
```

The β-Phaseolin promoter-AlMV leader fusion was digested with EcoRI and NcoI and the resulting 959 bp fragment was used in a three way ligation with the synthetic adaptors Lox 21/Lox 22 to clone into pUC18 linearized with EcoRI and KpnI.

pMOG426 (Example 2) was digested with HindIII and a synthetic adaptor (SEQ ID NOS 15 & 16, respectively):

```
Lox 4:      5'AGCTCGAGA 3'

Lox 5:      3'    GCTCTTCGA 5'
``` was cloned into this HindIII site creating a XhoI site downstream of the original HindIII site of the CruA terminator resulting in plasmid pMOG426*XhoI.

A cDNA clone of Lipoxygenase-3 (LOX-3) was isolated from soybean (Yenofsky et al., 1988, Isolation and characterisation of a soybean (Glycine max) lipoxygenase-3 gene, Mol. Gen. Genet 211: 215–222).

To fuse the 3' part of the LOX3 cDNA to the CruA terminator two synthetic oligo primers (SEQ ID NOS 17 & 18, respectively) were synthesized:

```
Lox 2:   5'AATCCCCAACAGTATCTCTATCTGAA 3'

Lox 3:   3'    GGGTTGTCATAGAGATAGACTTCTAG 5'
```

This adaptor destroys the 3' internal EcoRI site of LOX3 and creates a BglII site downstream of the stop codon.

The LOX3 cDNA was digested with EcoRI and the resulting 2.2 Kb fragment was used in a three way ligation with the oligo adapters Lox 2/Lox 3 and cloned into pMOG426*XhoI which was linearized with EcoRI and BglII. From the resulting vector a EcoRI-XhoI fragment (2468 bp) was cloned into pMOG800 linearized with EcoRI and XhoI. The resulting plasmid was used as a EcoRI digested vector to clone in the 1003 bp EcoRI-KpnI fragment (containing the fusion of β-Phaseolin, AlMV leader, and 5'-LOX-3) and the 289 bp KpnI-EcoRI isolated from the LOX3 cDNA clone. The resulting plasmid was designated pMOG1011.

The binary vector was finally transferred to *Agrobacterium tumefaciens* strain MOG 101 (Hood et al. 1993, Transgenic Res. 2: 208–218).

Transgenic *Arabidopsis thaliana* cv. C24 plants were generated by *Agrobacterium* mediated transformation as described (Valvekens et al., 1988, Proc. Natl. Acad. Sci. 85: 5536–5540).

S1-seed batches of L8 primary transformers transgenic for pMOG1219 were analysed for the expression of LOX-3 by Western analysis. Polyclonal antibodies against pea lipoxygenases 2 and 3 were raised in rabbits and obtained from Carlsberg laboratories (Copenhagen, DK). A sample of the antiserum was obtained. The antiserum crossreacts with soybean LOX-1 and LOX-3 but not with soybean LOX-2.

Transgenic seeds were homogenized in 50 mM sodium phosphate buffer, pH 7.5, containing 10 mM EDTA, 50 mM NaCl and 0.1% Triton X-100. The extracts were clarified by centrifugation for 5–10 minutes in an Eppendorf centrifuge. Twenty µg protein was loaded on a 12.5% SDS-PAA gel. The level of LOX-3 in the transgenic seed batches was compared to the expression level of the protein in a soybean mutant lacking LOX-1 but expressing both LOX-2 and LOX-3 at wild type levels (Wang et al. 1994, Proc. Natl. Acad. Sci. 91: 5828–5832) The expression level was approximately 100–200 times lower than in the mutant soybean.

EXAMPLE 9

Expression of Cyclodextrin Glucano-transferase in *Arabidopsis* Seeds

A cDNA clone encoding cyclodextrin glucano-transferase (CGTase) from *Bacillus circulans* strain 251 (Lawson et al. 1994, J. Mol. Biol. 236, 590–600) was obtained from Dr. L. Dijkhuizen (State University Gronngen). A binary expression construct, pMOG1160, [Cru-A (promoter)-Ω+4 (leader)-PR-S (signal peptide)-CGTase (coding sequence)-Cru-A (terminator)] was generated. The backbone of the binary expression construct is the binary vector pMOG800 harbouring between the left and right T-DNA borders the NPTII gene under control of the Nos promoter and multiple cloning sites.

The cloning of pMOG1160 took place as follows:

A 101 bp SalI-PvuII fragment of the CruA promoter (Example 2 this patent) was isolated and cloned with oligo primers (Cru-Omega I/Cru-Omega II), containing the complete Omega- +4 leader (Downson Day et al., Plant Mol. Biol. (1993) 23, 97–109) and part of the CruA promoter into the cloning vector pUC28 (see above) linearized with SalI and NcoI (SEQ ID NOS 19 & 20 respectively).

```
Cru-Omega I:
5' CTGTAAGACCAGACACGTATTTTTACAACAATTACCAACAACAACAAACAACAAACAACATTACAATTACTATTTACAATTAC 3'

Cru-Omega II:
5' CATGGTAATTGTAAATAGTAATTGTAATGTTGTTTGTTGTTTGTTGTTGTTGGTAATTGTTGTAAAAATACGTGTCTGGTCTTACAG 3'
```

From this fusion a 86 bp SalI-NcoI fragment was isolated and cloned with two oligo primers (Trans I/Trans II) containing the complete PR-S signal sequence (SEQ ID NOS 21 & 22, respectively):

```
Trans T:
5'CATGAACTTCCTCAAGAGCTTCCCCTTTTATGCCTTCCT
TTGTTTTGGCCAATACTTTGTAGCTGTTACGCATG        3'

Trans II:
5'CGTAACAGCTACAAAGTATTGGCCAAAACAAAGGAAG
GCATAAAAGGGGAAGCTCTTGAGGAAGTT              3'
``` into pUC18 linearized with SalI-SphI, this vector was designated pTCV210.

A cDNA clone encoding cyclodextrin glucano-transferase (CGTase) from *Bacillus circulans* strain 251 (Lawson et al. 1994, Nucleotide sequence and X-Ray structure of Cyclodextrin Glycosyltransferase from *Bacillus circulans* strain 251 in a maltose-dependent crystal form. J. Mol. Biol. 236, 590–600) was obtained from Dr. L. Dijkhuizen (State University Groningen). This cDNA clone was used as a template in a PCR reaction with the primers (SEQ ID NOS 2 & 24, respectively):

```
CGT-CGT-9    5'GCCCTGCGCATGCTGCGCCGGATACC 3'

CGT-CGT-8    5'GGAAGATCTTATGGCTGCCAATTCACGT 3'
```

These primers will create a SphI site just upstream of the mature CGTase gene and a BglII site directly downstream of the stop codon. The resulting 2082 bp PCR product was digested with SphI and BglII and cloned by a three way ligation together with the previously described CruA-Omega+4-PRS signal fragment (246 bp) digested with SalI-SphI into the cloning vector pUC28 linearized with SalI-BglII. The resulting plasmid was digested with a SalI and BglII and the 2328 bp fragment was isolated and ligated with a 218 bp BglII-HindIII fragment isolated from pMOG426 (see above) containing the CruA terminator into pUC18 linearized with SalI-HindIII. This vector was used to isolate the 2546 bp SalI-HindIII fragment and cloned together with the 5' part of the CruA promoter as a EcoRI-SalI fragment into pMOG800 linearized with EcoRI and HindIII resulting in pMOG1160.

The binary vector was finally transferred to *Agrobacterium tumefaciens* strain MOG 101 (Hood et al. 1993, Transgenic Res. 2: 208–218).

Transgenic *Arabidopsis thaliana* cv. C24 plants were generated by *Agrobacterium* mediated transformation as described (Valvekens et al., 1988, Proc. Natl. Acad. Sci. 85, 5536–5540).

S1 seed batches of primary *Arabidopsis* transformants transgenic for pMOG1160 were analysed for the expression of CGTase by Western analysis. As a standard, purified CGTase (Penniga et al. 1995, Biochemistry 34: 3368–3376) in a wild type protein background was included. The (polyclonal) antiserum that was used for the analysis was raised in rabbits against purified protein and was obtained from Lubbert Dijkhuizen, State University Groningen.

Transgenic seeds were homogenised in 50 mM sodium phosphate buffer, pH 7.5, containing 10 mM EDTA, 50 mM NaCl and 0.1% Triton X-100. The extracts were clarified by centrifugation for 5–10 minutes in an Eppendorf centrifuge. Ten µg protein was loaded on a 12.5% SDS-PAA gel. The level of CGT-ase expression varied between 0 and 2–3% based on total soluble protein.

EXAMPLE 10

Expression of Xylanase in Rice Seeds

A binary expression construct, pMOG1346 [glutelin (promoter)–Actin1 (leader+intron)–synthetic XlnA (coding region)–glutelin (terminator)] was generated harbouring the synthetic XlnA coding region under control of the rice glutelin promoter and rice glutelin terminator sequences. The actin leader and glutelin signal peptide were included in the construct as well. The backbone of this expression construct is the binary vector pMOG1006 harbouring between the left and right T-DNA borders the HPTII gene under control of the 35S CaMV promoter and multiple cloning sites.

A cDNA clone encoding the endoxylanase from *Aspergillus niger* (XlnA) has been described in the literature (de Graaff et al., 1994, Mol. Microbiol. 12: 479–490).

Based on the sequence of this cDNA clone and the sequence of the rice glutelin signal peptide a synthetic Gt1-XlnA gene fusion was constructed. The codon usage of the synthetic gene was adapted to what is expected to be optimal for translation effieciency in monocotelydenous plants. At the ATG of the synthetic Gt1-XlnA gene a NcoI site was created and 3' of the TGA stop codon a BamHI site was introduced. The synthetic gene was subcloned into the cloning vector pUC28 (see above) linearized with BamHI and NcoI and the correct sequence was confirmed by sequencing of the entire gene.

The Glutelin 1 terminator was isolated by PCR using genomic DNA isolated from Oryza Sativa cv Taipei 309 as a template and the primers (SEQ ID NOS 25 & 26, respectively):

```
Bac-Gt1-05:   5'GCGCTAAGATCTCAATGCGGATAA 3'

Bac-Gt1-06:   5'CGACTCTAGAATTATATAAATTACTC 3'
```

The resulting 480 bp PCR fragment was digested with XbaI and BglII and cloned into the pUC28 Gt1-XlnA vector linearized with BamHI-XbaI, fusing the synthetic Gt1-XlnA to the Gt1 terminator.

The Actin1 leader and intron were isolated by PCR using the pAct1-D plasmid obtained from R. Wu (Zhang W. et al., Analysis of the Rice Act1 5' region activity in transgenic rice plants. The Plant Cell (1991) 3: 1155–1165) as a template and the primers (SEQ ID NOS 27 & 28, respectively) (Bak-Act-08/PZT-Act-06):

5'CCCAACGATATCACCACCACCACCACCACCTCCTCCCCCCTCG 3'

5'CGTCAGCCATCTTCTACCTAC 3'

From this PCR fragment a 551 bp EcoRV-NcoI fragment was isolated.

The 3'part of the Rice Glutilin promoter was isolated by PCR using the pGT1 plasmid obtain from N. Murai (ref.: Zheng Z. et al., 5' distal and proximal cis-acting regulator elements are required for developmental control of a rice seed storage protein glutelin gene. The Plant Journal (1993), 4: 357–366) as a template and the primers (SEQ ID NOS 29 & 30, respectively):

Bak-Gt1-09:   5'CGAGGTCGACGGTATCGATGACATAGC 3'

Bak-Gt1-10:   5'CTAATGAACTGATATCTTTTTGTGAG 3'

From this PCR fragment a 522 bp by EcoRV-ClaI fragment was isolated. This fragment and the previous EcoRV-NcoI actin leader fragment were cloned into pUC28 (see above) digested with NcoI-ClaI. From this plasmid a 1073 bp NcoI-ClaI fragment was isolated and cloned by a three way ligation with the 1107 bp KbaI-NcoI fragment containing the fusion of the synthetic Gt1-KlnA and Glutelin terminator into pUC28 linearized with XbaI and ClaI.

The remaining part of the rice glutelin promoter (approximately 4.5 Kb) was isolated from plasmid pTRA311 also obtained from N. Murai as a KpnI-ClaI fragment. This fragment and a XbaI-ClaI fragment from the previous plasmid were cloned into pMOG1006 linearized with XbaI and KpnI.

The binary vector was finally transferred to *Agrobacterium tumefaciens* strain EHA 105 (Hood et al. 1993, Transgenic Res. 2: 208–218).

Transgenic rice plants were generated by *Agrobacterium* mediated transformation as described (Hiei et al. (1994), The Plant Journal 6: 271–282).

Seed batches (S1) of primary rice transformants transgenic for pMOG1327 were analyzed for the expression of xylanase by using an activity assay as described (Maat. J. et al., 1992, Xylanases and their application in bakery In: Xylans and Xylanases, J. Visser ed., Elsevier Science Publishers B.V.). Seeds derived from transgenic plants showed an enhanced level of xylanase activity compared to the non-transgenic control samples.

While the present invention has been described with reference to specific embodiments thereof, it should be understood by those skilled in the art that various changes may be made and equivalents may be substituted without parting from the true spirit and scope of the invention. In addition, many modifications may be made to adapt a particular situation, material, plant, seed, process, process step or steps to the object, spirit and scope of the invention. All such modifications are intended to be within the scope of the claims appended hereto.

EXAMPLE 11

The Use of Endo-xylanase in Bread Making

Pup-loaves were baked from 150 g dough pieces obtained by mixing 200 g wheat flour (100%), 106 ml water (53%), 1.2 g instant dry baker's yeast (0.6%; Gist-brocades N.V., Delft, The Netherlands), 4 g NaCl (2%), 400 mg $CaCl_2.2H_2O$ (0.2%), 10 mg fungal α-amylase $P_{200}$ (Gist-brocades, 2250 SKB/kg flour) and a variable number of units of endo-xylanase (xyl A) activity. After mixing for 6 minutes and 15 seconds at 52 r.p.m. in a pin mixer, the dough was divided, proofed for 45 minutes at 31° C., punched, proofed for an additional 25 minutes, molded and panned. After a final proof of 70 minutes at 31° C., the dough was baked for 20 minutes in an oven at 250° C. Loaf volume was determined by the rapeseed displacement method. The results are summarized in the Table below.

TABLE 2

Characteristics of bread prepared with various amounts of endo-xylanase (xyl A) activity

| Xyal A activity Units | Leaf volume (ml) | Break/Shred* | Crumb Structure* |
|---|---|---|---|
| 0 | 546 | 6 | 6 |
| 32 | 560 | 7 | 6 |
| 128 | 579 | 7.5 | 7 |
| 320 | 609 | 8 | 6.5 |
| 640 | 621 | 7.5 | 6.5 |
| 960 | 624 | 7.5 | 7 |
| 2560 | 618 | 7.5 | 7.5 |

*= score from 1 (lowest quality) to 10 (highest quality)

References

Altenbach, S. B., Pearson, K. W., Meeker, G., Staraci, L. C. & Sun, S. S. M. (1989) Plant Mol. Biol. 13, 513.

Auffray & Rougeon (1980) Eur. J. Biochem. 107, 303–314.

Barker, S. J., Harada, J. J. & Goldberg, R. B. (1988) Proc. Natl. Acad. Sci. USA 85, 458.

Baulcombe, D. C., Saunders, G. R., Bevan, M. W., Mayo, M. A. & Harrison, B. D. (1986) Nature 321, 446.

Baumlein, H., Wobus, U., Pastell, J., & Kafatos, F. C. (1986) Nucl. Acids Res. 14, 2707.

Beachy, R. N., Chen, Z.-L., Horsch, R. B., Rogers, S. G., Hoffmann, N. J. & Fraley, R. T. (1985) EMBO J. 4, 3047.

Bevan, M. (1984) Nucl. Acids Res. 12, 8711.

Brederode, F. T., Koper-Zwarthoff, E. C. & Bol, J. F. (1980) Nucl.Acids Res 8, 2213.

Bustos, M. M., Guiltinan, M. J., Jordano, J., Begum, D., Kalkan, F. A. & Hall, T. C. (1989) Plant Cell 1, 839.

Casey, R. & Domoney, C. (1987) Plant Mol. Biol. Reporter 5, 261.

Chee, B. B., Klassy, R. C. & Slightom, J. L. (1986) Gene 41, 47.

Cornelissen, B. J. C., Hofft van Huijsduijnen, R. A. M. & Bol, J. F. (1986) Nature 321, 531.

Della-Cioppa, G., Kishore, G. M., Beachy, R. N. & Fraley, R. T. (1987) Plant Physiol. 84, 965.

Ditta, G., Stanfield, S., Corbin, D. & Helinski, D. R. (1980) Proc. Natl. Acad. Sci. USA 77, 7347.

Dorel, C., Voelker, T. A., Herman, E. M. & Chrispeels, M. J. (1989) J. Cell Biol. 108, 327.

Doyle, J. J., Schuler, M. A., Godette, W. D., Zenger, V., Beachy, R. N. & Slighom, J. L. (1986) J. Biol. Chem. 261, 9228.

Ellis, J. R., Shirsat, A. H., Hepher, A., Yarwood, J. N., Gatehouse, J. A., Croy, R. R. D. & Boulter, D. (1988) Plant Mol. Biol. 10, 203.

Fischer, R. L. & Goldberg, R. B. (1982) Cell 29, 651.

Fry, J. & Barnason, A. & Horsch, R. B. (1987) Plant Cell Reports 6, 321.

Gasser, C. S. & Fraley, R. T. (1989) Science 244, 1293.

Goodman, R. M., Knauf, V. C., Houck, C. M. & Comai, L. (1987) PCT/WO 87/00865.

Gordon-Kamm, W. J., Spencer, T. M., Mangano, M. L., Adams, T. R., Daines, R. J., Start, W. G., O'Brien, J. V., Chambers, S. A., Adams Jr., W. R., Willets, N. G., Rice, T. B., Mackey, C. J., Krueger, R. W., Kausch, A. P. & Lemaux, P. G. (1990) The Plant Cell 2, 603.

Guilley, H., Dudley, R. K., Jonard, G., Balazs, E. & Richards, K. E. (1982) Cell 30, 763.

Harada, J. J., Barker, S. J. & Goldberg, R. B. (1989) Plant Cell 1, 415.

Hattori, T., Nakagawa, T., Maeshima, M., Nakamura, K., & Asahi, T. (1985) Plant Mol. Biol. 5, 313.

Hiatt, A., Cafferkey, R. & Boedish, K. (1989) Nature 342, 76.

Higgins, T. J. V., (1984) Annu. Rev. Plant Physiol. 35, 191.

Higgins, T. J. V., Newbigin, E. J., Spencer, D., Llewellyn, D. J. & Craig, S. (1988) Plant Mol. Biol. 11, 683.

Hokema, A., Hirsch, P. R., Hooykaas, P. J. J. & Schilperoort, R. A. (1983) Nature 303, 179.

Hoffman, L. M., Donaldson, D. D., Bookland, R., Rashna, K. & Herman, E. M. (1987) EMBO J. 6, 3213.

Horsch, R. B., Fry, J. E., Hoffmann, N. L., Eichholtz, D., Rogers, S. G. & Fraley, R. T. (1985) Science 227, 1229.

Iturriaga, G., Jefferson, R. A. & Bevan, M. W. (1989) Plant Cell 1, 381.

Jefferson, R. A. (1987) Plant Mol. Biol. Reporter 5, 387.

Jordano, J., Almoguera, C. & Thomas, T. L. (1989) Plant Cell 1, 855.

Kay, R., Chan, A., Dayly, M. & McPherson, J. (1987) Science 236, 1299.

Klee, H., Horsch, R. & Rogers, S. (1987) Annu. Rev. Plant Physiol. 38, 467.

Krebbers, E. & Vandekerckhove, J. (1990) TIBTECH, 8, 1.

Larkins, M. A. (1981) In: *The biochemistry of plants* Vol. 6 (Academic Press, San Diego: Stumpf, P. K. & Conn, E. E., eds.). Chapter 11. p. 471.

Lee, B., Murdoch, K., Topping, J., Kreis, M. & Jones, M. G. K. (1989) Plant Mol. Biol. 13, 21.

Lycett, G. W., Delauney, A. J., Gatehouse, J. A., Gilroy, J., Croy, R. R. D. & Boulter, D. (1983) Nucl. Acids Res. 11, 2367.

Lycett, G. W., Croy, R. R. D., Shirsat, A. H. & Boulter, D. (1984) Nucl. Acids Res. 12, 4493.

Mariani, C., de Beuckeleer, M., Truettner, J., Leemans, J., & Goldberg, R. B. (1990) Nature 347, 737.

Marsh, J. L., Erfle, M. & Wykes, E. J. (1984) Gene 32, 481.

Mettler, I. J. (1987) Plant Mol. Biol. Rep. 5, 346.

Okamura, J. K., Jokufu, K. D. & Goldberg, R. B. (1986) Proc. Natl. Acad. Sci. USA 83, 8240.

Pang, P. P., Pruitt, R. E. & Meyerowitz, E. M. (1988) Plant Mol. Biol. 11, 805.

Potrykus, I. (1990) Bio/Technol. 8, 535.

Radke, S. E., Andrews, B. M., Moloney, M. M., Crough, M. L., Kridl, J. C. & Knauf, V. C. (1988) Theor Appl. Genet. 75, 685.

Reilly, P. J. (1985) In: *Starch Conversion Technology* (Marcel Dekker, Inc., New York: Van Beynum, G. M. A. & Roels, J. A., eds.), Chapter 5, p. 101.

Riggs, C. D., Hunt, D. C., Lin, J. & Chrispeels, M. J. (1989) Plant Sci. 63, 47.

Rodenburg, K. W., DeGroot, M. J. A., Schilperoort, R. A. & Hooykaas, P. J. J. (1989) Plan Mol. Biol., 13, 711.

Ryan, A. J., Royal, C. L., Hutchinson, J. & Shaw, C. H. (1989) Nucl. Acids Res. 17, 3584.

Scofield, S. R. & Crouch, M. L. (1987) J. Biol. Chem. 262, 12202.

Schilperrort, R. A., Hoekema, A. & Hooykaa, P. J. J. (1984) European Patent Application No. 0 120 516.

Sengupta-Gopalan, C., Reichert, N. A., Barker, R. F., Hall, T. C. & Kemp, J. D. (1985) Proc. Natl. Acad. Sci. USA 82, 3320.

Shimamoto, K., Terada, R., Izawa, T. & Fujimoto, J. (1989) Nature 338, 274.

Shotwell, M. A. & Larkins, B. A. (1989) In: *The biochemistry of plants* Vol. 15 (Academic Press, San Diego: Stumpf, P. K. & Conn, E. E., eds.). Chapter 7. p. 297.

Sijmons, P. C., Dekker, B. M. M., Schrammeijer, B., Verwoerd, T. C., van den Elzen, P. J. M. & Hoekema, A. (1990) Bio/Technol. 8, 217.

Slightom, J. L., Schaber, M. D. & Kramer, R. A. (1986) In: *Molecular biology of seed storage proteins and lectins* (Waverly Press, Baltimore: Shannon, L. M. & Chrispeels, M. J., eds.) Am. Soc. Plant Physiol. p. 183.

Smith, J. J. & Raikhel, N. V. (1989) Plant Mol. Biol. 13, 601.

Vaara, T., Vaara, M., Simell, M., Lehmussaari, A. & Caransa, A. (1989) European Patent Application 0 321 004.

Vandekerckhove, J., VanDamme, J., VanLijsebettens, M., Botterman, J., DeBlock, M., DeClerq, A., Leemans, J., Van Montagu, M. & Krebbers, E. (1989) Bio/Technol. 7, 929.

van Gorcom, R. F. M., van Hartingsveldt, W., van Paridon, P. A., Veenstra, A. E., Luiten, R. G. M., Selten, G. C. M. (1991) European Patent Application 89202436.5, Publication No. 0 420 358, filed Sep. 27, 1989.

Vasil, V., Redway, F. & Vasil, I. K. (1990) Bio/Technol. 8, 429.

Vitale, A. & Bollini, R. (1986) In: *Molecular biology of seed storage proteins and lectins* (Waverley Press, Baltimore: Shannon, L. M. & Chrispeels, M. J., eds.) Am. Soc. Plant Physiol. P. 175.

Voelker, T. A., Herman, E. M. & Chrispeels, M. J. (1989) Plan Cell 1, 95.

Vonder Haar, R. A., Allen, R. D., Cohen, E. A., Nessler, C. L. & Thomas, T. L. (1988) Gene 74, 433.

What is claimed is:

1. A flour which comprises the substrate for a bakery enzyme, which flour also comprises ground seeds of a transgenic plant comprising an expression construct which comprises a nucleic acid sequence encoding said bakery enzyme in the seeds of the plant, wherein said bakery enzyme is heterologous to said seeds, and wherein said enzyme is functionally expressed in said seeds.

2. A bakery dough which comprises the substrate for a bakery enzyme, which flour also comprises ground seeds of a transgenic plant comprising an expression construct which comprises a nucleic acid sequence encoding said bakery enzyme in the seeds of the plant, wherein said bakery enzyme is heterolgous to said seeds, and wherein said enzyme is functionally expressed in said seeds wherein the bakery enzyme is selected from the group consisting of lipoxygenase, xylanase, protein disulfide isomerase, and cyclodextrin glycosyl-transferase.

3. The flour according to claim 1 wherein the seeds are seeds of *Nicotiana, Brassica, Arabidopsis* or *Oryza*.

4. The flour according to claim 1 wherein the seeds are seeds of *Zea, Glycine, Hordeum, Triticum, Medicago, Phaseolus*, or *Pisum*.

5. The flour according to claim 1 wherein the bakery enzyme is selected from the group consisting of phytase, lipoxygenase, xylanase, protein disulfide isomerase, and cyclodextrin glycosyl-transferase.

* * * * *

SEQUENCE LISTING

<160> NUMBER OF SEQ ID NOS: 50

<210> SEQ ID NO 1
<211> LENGTH: 28
<212> TYPE: DNA
<213> ORGANISM: Artificial Sequence
<220> FEATURE:

```
<223> OTHER INFORMATION: Description of Artificial Sequence: Synthetic
      oligo adaptor

<400> SEQUENCE: 1
aattcagatc tccatggatc gatgagct                                          28

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligo adaptor

<400> SEQUENCE: 2
catcgatcca tggagatctg                                                   20

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 3
ctgtaagacc agagggtttt tattttaat tttctttcac ctaggtccac                   50

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 4
catggtggac ctaggtgaaa gaaaattaaa aataaaaacc ctctggtctt acag             54

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
cgcaccatgg tgtggacact g                                                 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
cttgaatatt ctttccacca t                                                 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
ccaaccatgg cgaaaaacgt t                                                 21
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
ccacaccatg gtgcgtagaa ctcaacgacg          30

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
gacatcatag aattcattga a          21

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
gcggagatct tcaaagctca tcttttgg          28

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
gcgcgaattc tatacaatga aaatttcacc          30

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
gctctcacca tggtagagta g          21

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 13
catgcttggg ggtcttctcc atagggtca taagataaaa ggtac          45

<210> SEQ ID NO 14
<211> LENGTH: 37
<212> TYPE: DNA
<213> ORGANISM: Artificial Sequence

```
<220> FEATURE:
<223> OTHER INFORMATION: Description of Artificial Sequence: Synthetic
      adaptor

<400> SEQUENCE: 14
cttttatctt atgaccccta tggagaagac ccccaag                            37

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 15 agctcgaga                                                           9

<210> SEQ ID NO 16
<211> LENGTH: 9
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 16 agcttctcg                                                           9

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
aatccccaac agtatctcta tctgaa                                        26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 18
gatcttcaga tagagatact gttggg                                        26

<210> SEQ ID NO 19
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 19
ctgtaagacc agacacgtat ttttacaaca attaccaaca acaacaaaca acaaacaaca   60
ttacaattac tatttacaat tac                                           83

<210> SEQ ID NO 20
<211> LENGTH: 87
<212> TYPE: DNA
<213> ORGANISM: Artificial Sequence
<220> FEATURE:
<223> OTHER INFORMATION: Description of Artificial Sequence: Primer
```

```
<400> SEQUENCE: 20
catggtaatt gtaaatagta attgtaatgt tgtttgttgt ttgttgttgt tggtaattgt     60
tgtaaaaata cgtgtctggt cttacag                                        87

<210> SEQ ID NO 21
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 21
catgaacttc ctcaagagct tcccctttta tgccttcctt tgttttggcc aatactttgt    60
agctgttacg catg                                                      74

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 22
cgtaacagct acaaagtatt ggccaaaaca aggaaggca taaaggggga agctcttgag     60
gaagtt                                                               66

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
gccctgcgca tgctgcgccg gatacc                                         26

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 24
ggaagatctt atggctgcca attcacgt                                       28

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
gcgctaagat ctcaatgcgg ataa                                           24

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 26
cgactctaga attatataaa ttactc                                              26

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 27
cccaacgata tcaccaccac caccaccacc tcctcccccc tcg                           43

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
cgtcagccat cttctaccta c                                                   21

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 29
cgaggtcgac ggtatcgatg acatagc                                             27

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 30
ctaatgaact gatatctttt tgtgag                                              26

<210> SEQ ID NO 31
<211> LENGTH: 642
<212> TYPE: DNA
<213> ORGANISM: Bacillus licheniformis
<220> FEATURE:
<221> NAME/KEY: CDS
<222> LOCATION: (7)..(630)

<400> SEQUENCE: 31

```
catgcc atg gca tcc ata aat cgc ccc ata gtt ttc ttc aca gtt tgc           48
       Met Ala Ser Ile Asn Arg Pro Ile Val Phe Phe Thr Val Cys
         1               5                  10 ttg ttc ctc ttg tgc gat ggc tcc cta gcc tca gcg gga atc aac tac           96
Leu Phe Leu Leu Cys Asp Gly Ser Leu Ala Ser Ala Gly Ile Asn Tyr
 15                  20                  25                  30 gtc cag aac tac aat ggc aac ctc ggc gac ttt act tac gac gag tca          144
Val Gln Asn Tyr Asn Gly Asn Leu Gly Asp Phe Thr Tyr Asp Glu Ser
                 35                  40                  45 gcg gga act ttc agc atg tat tgg gag gat ggc gtg tcc tca gac ttc          192
Ala Gly Thr Phe Ser Met Tyr Trp Glu Asp Gly Val Ser Ser Asp Phe
             50                  55                  60
```

```
gtc gtg gga ctg ggc tgg acc act gga tca tcc aat gcg atc acc tac    240
Val Val Gly Leu Gly Trp Thr Thr Gly Ser Ser Asn Ala Ile Thr Tyr
            65                  70                  75 agc gcc gag tac tcc gcg tca gga tca gcc tcc tat ctg gcc gtg tac    288
Ser Ala Glu Tyr Ser Ala Ser Gly Ser Ala Ser Tyr Leu Ala Val Tyr
 80                  85                  90 gga tgg gtg aac tac ccg cag gcc gag tac tac atc gtg gag gat tac    336
Gly Trp Val Asn Tyr Pro Gln Ala Glu Tyr Tyr Ile Val Glu Asp Tyr
 95                 100                 105                 110 gga gat tac aac cca tgc agc tca gcg acc tcc ctc gga act gtg tac    384
Gly Asp Tyr Asn Pro Cys Ser Ser Ala Thr Ser Leu Gly Thr Val Tyr
                115                 120                 125 agc gac ggc tcc acc tac cag gtc tgc acc gac acc cgc act aac gag    432
Ser Asp Gly Ser Thr Tyr Gln Val Cys Thr Asp Thr Arg Thr Asn Glu
            130                 135                 140 ccg tca atc acc ggc act tcc acc ttc acc cag tac ttc agc gtg cgc    480
Pro Ser Ile Thr Gly Thr Ser Thr Phe Thr Gln Tyr Phe Ser Val Arg
        145                 150                 155 gag tcc act cgc acc tca gga acc gtg acc gtc gcg aac cac ttc aac    528
Glu Ser Thr Arg Thr Ser Gly Thr Val Thr Val Ala Asn His Phe Asn
    160                 165                 170 ttc tgg gcg cag cac gga ttc ggc aac agc gac ttt aac tac cag gtg    576
Phe Trp Ala Gln His Gly Phe Gly Asn Ser Asp Phe Asn Tyr Gln Val
175                 180                 185                 190 gtc gca gtg gag gca tgg tca gga gcg ggc tca gcg tcc gtc act atc    624
Val Ala Val Glu Ala Trp Ser Gly Ala Gly Ser Ala Ser Val Thr Ile
                195                 200                 205 agc tcc tgaggatccg cg                                              642
Ser Ser

<210> SEQ ID NO 32
<211> LENGTH: 208
<212> TYPE: PRT
<213> ORGANISM: Bacillus licheniformis

<400> SEQUENCE: 32

Met Ala Ser Ile Asn Arg Pro Ile Val Phe Thr Val Cys Leu Phe
 1               5                  10                  15

Leu Leu Cys Asp Gly Ser Leu Ala Ser Ala Gly Ile Asn Tyr Val Gln
                 20                  25                  30

Asn Tyr Asn Gly Asn Leu Gly Asp Phe Thr Tyr Asp Glu Ser Ala Gly
                35                  40                  45

Thr Phe Ser Met Tyr Trp Glu Asp Gly Val Ser Ser Asp Phe Val Val
    50                  55                  60

Gly Leu Gly Trp Thr Thr Gly Ser Ser Asn Ala Ile Thr Tyr Ser Ala
 65                  70                  75                  80

Glu Tyr Ser Ala Ser Gly Ser Ala Ser Tyr Leu Ala Val Tyr Gly Trp
                 85                  90                  95

Val Asn Tyr Pro Gln Ala Glu Tyr Tyr Ile Val Glu Asp Tyr Gly Asp
            100                 105                 110

Tyr Asn Pro Cys Ser Ser Ala Thr Ser Leu Gly Thr Val Tyr Ser Asp
        115                 120                 125

Gly Ser Thr Tyr Gln Val Cys Thr Asp Thr Arg Thr Asn Glu Pro Ser
    130                 135                 140

Ile Thr Gly Thr Ser Thr Phe Thr Gln Tyr Phe Ser Val Arg Glu Ser
145                 150                 155                 160

Thr Arg Thr Ser Gly Thr Val Thr Val Ala Asn His Phe Asn Phe Trp
                165                 170                 175
```

```
Ala Gln His Gly Phe Gly Asn Ser Asp Phe Asn Tyr Gln Val Val Ala
            180                 185                 190

Val Glu Ala Trp Ser Gly Ala Gly Ser Ala Ser Val Thr Ile Ser Ser
        195                 200                 205

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttcggaatt cgggttccgg                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aactgttgag ctgtagagcc                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cttaagatct tacccagtga                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cggagaagct tgcatctcgt                                                   20

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Polylinker
      sequence

<400> SEQUENCE: 37
ggaattctgg tacctcccgg gaggatccat ctagagctcg agtaagcttc                  50

<210> SEQ ID NO 38
<211> LENGTH: 3113
<212> TYPE: DNA
<213> ORGANISM: Brassica napus

<400> SEQUENCE: 38
```

-continued

```
tatttacgtt cggtcggata acggacgggt tttcagttcg ggttcggttc ggatttcggg      60
ttccggattt atatggccct agcctaaatt cgagtgtgac cgttaatccg ttatactacg     120
atctaatcaa acatgtctta gatcaaattt gcaatcttat tgcatatttt tttgtctaac     180
aatattacta gaaatctttg tttattacca acattagtaa aactatatct taaccaaagt     240
tgcaggagca gttcgtttca aacgtaattg ctatagtgat gttattgtaa atttgttata     300
ctgatcaaat gtaaagaata atacaatttt atatatatct gacaaacaaa tcagtatata     360
tatacaagaa atatatattt tgtcctatta catatgccta tctcaaagtt gatgtgtaaa     420
gacatgcagt tcaataagcc atgcaaattg agatgtgtca aactcccttc gttaatatgt     480
gttttcttac aatgtgaagc caaattaaat tttcagaaga agacataaag atagcaactc     540
aaatgaagtg tagattgtac atagtcgact ctatatacct ggttcttatc tcattcaatt     600
tatcctcaaa aaaatttatc aacatctata caaataagtt cactataaat agcttcatct     660
aactcagctg taagaccaga aaaccacaa caactaagta aagagaaaat ggctcggctc     720
tcatctcttc tctctttttc cttagcactt ttgacttttc tccatggctc tacagctcaa     780
cagtttccaa acgagtgtca gctagaccag ctcaatgcac tggagccgtc acacgtactt     840
aaggctgagg ctggtcgcat cgaggtgtgg gaccaccacg ctcctcagct acgttgctct     900
ggtgtctcct ttgtacgtta catcatcgag tctaagggtc tctacttgcc ctctttcttt     960
agcaccgcga ggctctcctt cgtggctaaa ggtacgtgaa tctgattttg atactatatg    1020
agtatcgaga ttcaaattcg tgatctttaa ggttcagtct tttgagaaaa gtgttgtagt    1080
aagtatatca ctatacacgt gctaaggttt tgatcaaata cattataata ttttttttgtt   1140 taatttataa cctaaatata tggtcgatgt tcacagaact gcgcactaaa ttttttttt    1200 ttggtttgtt acattatagg agaaggtctt atggggagag tggtcttgtg cgccgagaca    1260
ttccaggact catcagtgtt tcaaccaagc ggtggtagcc ccttcggaga aggtcagggc    1320
caaggacaac aaggtcaggg ccaaggccac caaggtcaag gccaaggaca acagggccaa    1380
caaggtcagc aaggacaaca gagtcaaggc cagggtttcc gtgatatgca ccagaaagtg    1440
gagcacataa ggactgggga caccatcgct acacatcccg gtgtagccca atggttctac    1500
aacgacggaa accaaccact tgtcatcgtt tccgtcctcg atttagccag ccaccagaat    1560
cagctcgacc gcaacccaag ggtatataaa taaacaaaaa cctcaaaagc aatcaagggc    1620
aaatctcctt tttagcatat ttctaaattt atatcacaaa aatagcaatc aaaaactaaa    1680
atgaccaaaa tcatactttt ctaagtttat cctttgaaaa ttttaatttt tttatttttc    1740
aaatttgaat ctatacgccc aaacctcatt tctcaaccct aaaccataac cctaatctaa    1800
accttaaacc ctaaaccca aaccctaaac cctaaaccct aaatcctaaa ccccagcctt    1860
aaactctaaa ccctaaaccc taagtttgtg acttttgata aaacattaag tgctattttg    1920
tgactttgac cttggtgcta gtttgagaac ataaacttga tttagtgcta ttttttgtctt    1980 tttctcatca tataacttct tttataatta cagaatatca aaaatatggt tttctgttt    2040 atctgtagcc attttactta gccggaaaca acccacaagg ccaagtatgg atagaaggac    2100
gcgagcaaca gccacaaaag aacatcctta atggcttcac accagaggtt cttgctaaag    2160 cttttcaagat cgatgttagg acagcgcaac aacttcagaa ccagcaagac aaccgtggaa    2220
acattatccg agtccaaggc ccattcagtg tcattaggcc gcctttgagg agtcagagac    2280
cgcaggagga agttaacggt ttagaagaga ccatatgcag cgcgaggtgc accgataacc    2340
```

```
tcgatgaccc atctaatgct gacgtataca agccacagct cggttacatc agcactctga      2400
acagctatga tctccccatc cttcgcttcc ttcgtctctc agccctccgt ggatctatcc      2460
gtcaaaacgc gatggtgctt ccacagtgga acgcaaacgc aaacgcggtt ctctacgtga      2520
cagacgggga agcccatgtg caggtggtta acgacaacgg tgacagagtg ttcgacggac      2580
aagtctctca aggacagcta ctttccatac cacaaggttt ctccgtggtg aaacgcgcaa      2640
caagcgaaca gttccggtgg atcgagttca agacaaacgc aaacgcacag atcaacacac      2700
ttgctggacg aacctcggtc ttgagaggtt taccattaga ggtcatatcc aatgggtacc      2760
aaatctcact cgaagaagca agaagggtta agttcaacac gatcgagacc actttgacgc      2820
acagcagtgg cccagctagc tacggagggc caaggaaggc tgatgcttaa gagcttaccc      2880
agtgaacctc tactgtaaaa ggaagttaaa tagtaataaa aagagtaata ataatgtacg      2940
caaatgtgac tggttttgta gaggttttag aatgttactc cttttctgaa taaataact       3000 cttttctatc aaggtttagc tagctgggct aatctatcaa cttcattttt cgactacgtc      3060
tacacatacg tatacgagat gcaggcttct ccgaggatat agtgacagta tct             3113

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 gggttttat tttaattttt ctttcaaata cttccaccat gggtaacgga tcca                54

<210> SEQ ID NO 40
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agcttggatc cgttacccat ggtggaagta tttgaaagaa aattaaaaat aaaaaccc           58

<210> SEQ ID NO 41
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
catgaacttc ctcaagagct tccccttttta tgccttcctt tgttttggcc aatactttgt        60
agctgttacg catgctcgag                                                     80

<210> SEQ ID NO 42
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gatcctcgag catgcgtaac agctacaaag tattggccaa acaaaggaa ggcataaaag          60
```

```
gggaagctct tgaggaagt                                                 79
```

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
ctctggcagt ccccgcctcg agcccctgc ag                                   32
```

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
gatcctgcag ggggctcgag gcggggactg ccagagcatg                          40
```

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
His Gly Ser Thr Ala Leu Ala Val Pro Ala Ser
1               5                   10
```

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
catggctcta cagctctggc agtccccgcc tcgaggatat cctgcagatc tcccca        56
```

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
agcttgggga gatctgcagg atatcctcga ggcggggact gccagagctg tagagc        56
```

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

-continued

```
ctgcaaatct taatgggacg ctgatg                                      26

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tactgcatca gcgtcccatt aagatttgca gcatg                            35

<210> SEQ ID NO 50
<211> LENGTH: 1777
<212> TYPE: DNA
<213> ORGANISM: Bacillus licheniformis

<400> SEQUENCE: 50
tctagagtca tgaaacaaca aaaacggctt tacgcccgat tgctgacgct gttatttgcg    60
ctcatcttct tgctgcctca ttctgcagca gcggcggcaa atcttaatgg gacgctgatg   120
cagtattttg aatggtacat gcccaatgac ggccaacatt ggaagcgttt gcaaaacgac   180
tcggcatatt tggctgaaca cggtattact gccgtctgga ttccccggc  atataaggga   240 acgagccaag cggatgtggg ctacggtgct tacgacctt  atgatttagg ggagtttcat   300
caaaaaggga cggttcggac aaagtacggc acaaaaggag agctgcaatc tgcgatcaaa   360
agtcttcatt cccgcgacat taacgtttac ggggatgtgg tcatcaacca caaaggcggc   420
gctgatgcga ccgaagatgt aaccgcggtt gaagtcgatc ccgctgaccg caaccgcgta   480
atttcaggag aacacctaat taaagcctgg acacattttc attttccggg gcgcggcagc   540
acatacagcg atttttaaatg gcattggtac cattttgacg gaaccgattg ggacgagtcc   600
cgaaagctga accgcatcta taagtttcaa ggaaaggctt gggattggga agtttccaat   660
gaaaacggca actatgatta tttgatgtat gccgacatcg attatgacca tcctgatgtc   720
gcagcagaaa ttaagagatg gggcacttgg tatgccaatg aactgcaatt ggacggtttc   780
cgtcttgatg ctgtcaaaca cattaaattt tctttttttgc gggattgggt taatcatgtc   840
agggaaaaaa cggggaagga aatgtttacg gtagctgaat attggcagaa tgacttgggc   900
gcgctggaaa actatttgaa caaaacaaat tttaatcatt cagtgtttga cgtgccgctt   960
cattatcagt tccatgctgc atcgacacag ggaggcggct atgatatgag gaaattgctg  1020
aacggtacgg tcgttccaa  gcatccgttg aaatcggtta catttgtcga taaccatgat  1080
acacagccgg ggcaatcgct tgagtcgact gtccaaacat ggtttaagcc gcttgcttac  1140
gcttttattc tcacaaggga atctggatac cctcaggttt tctacgggga tatgtacggg  1200
acgaaaggag actcccagcg cgaaattcct gccttgaaac acaaaattga accgatctta  1260
aaagcgagaa acagtatgc  gtacggagca cagcatgatt atttcgacca ccatgacatt  1320
gtcggctgga caagggaagg cgacagctcg gttgcaaatt caggtttggc ggcattaata  1380
acagacggac ccgtgggggc aaagcgaatg tatgtcggcc ggcaaaacgc cggtgagaca  1440
tggcatgaca ttaccggaaa ccgttcggag ccggttgtca tcaattcgga aggctgggga  1500
gagtttcacg taaacggcgg gtcggtttca atttatgttc aaagatagaa gagcagagag  1560
gacggatttc ctgaaggaaa tccgtttttt tattttgccc gtcttataaa tttcttgat   1620 tacatttat  aattaatttt aacaaagtgt catcagccct caggaaggac ttgctgacag  1680
```

-continued

```
tttgaatcgc ataggtaagg cggggatgaa atggcaacgt tatctgatgt agcaaagaaa    1740
gcaaatgtgt cgaaaatgac ggtatcgcgg gtgatca                             1777
```